US008134031B2

(12) United States Patent
Peng (10) Patent No.: US 8,134,031 B2
(45) Date of Patent: Mar. 13, 2012

(54) EXTRACTION PROCESS FOR ALDEHYDE PRODUCT SEPARATION AND CATALYST RECOVERY

(75) Inventor: Wei-Jun Peng, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 160 days.

(21) Appl. No.: 12/664,220

(22) PCT Filed: May 30, 2008

(86) PCT No.: PCT/US2008/065261
§ 371 (c)(1),
(2), (4) Date: Apr. 16, 2010

(87) PCT Pub. No.: WO2008/156993
PCT Pub. Date: Dec. 24, 2008

(65) Prior Publication Data
US 2010/0228057 A1  Sep. 9, 2010

Related U.S. Application Data

(60) Provisional application No. 60/934,391, filed on Jun. 13, 2007.

(51) Int. Cl.
*C07C 45/78* (2006.01)
*C07C 45/50* (2006.01)
(52) U.S. Cl. ..................................... 568/420; 568/454
(58) Field of Classification Search .................. 568/420, 568/454
See application file for complete search history.

(56) References Cited

U.S. PATENT DOCUMENTS

| 3,787,459 A | 1/1974 | Frankel |
| 4,483,802 A | 11/1984 | Gartner et al. |
| 4,633,021 A | 12/1986 | Hanes |
| 4,731,486 A | 3/1988 | Abatjoglou et al. |
| 5,180,854 A | 1/1993 | Abatjoglou et al. |
| 7,663,002 B2 * | 2/2010 | Peng et al. ..................... 568/454 |
| 2006/0089511 A1 | 4/2006 | Baranski |

FOREIGN PATENT DOCUMENTS

| FR | 2328069 A1 | 5/1977 |
| GB | 2276832 A | 10/1994 |
| JP | 09227129 A | 9/1997 |
| WO | WO-2004/096744 A2 | 11/2004 |
| WO | WO-2004/096882 A1 | 11/2004 |
| WO | WO-2006/012344 A1 | 2/2006 |
| WO | WO-2007035540 A2 | 3/2007 |
| WO | WO-2007/133379 A1 | 11/2007 |

OTHER PUBLICATIONS

Abstracts of Papers, 223$^{rd}$ ACS National Meeting, Orlando, FL, United States, Apr. 7-11, 2002, ORGN-392 "Recovery and reuse of rhodium catalyst in the hydroformylation of vegetable oils." Petrovic, Zoran; Kandanarachchi, Pramod. Kansas Polymer Research Center, Pittsburg, KS, SA. Publisher: American Chemical Society, Washington, D.C.
Abstracts of Papers, 223$^{rd}$ ACS National Meeting, Orlando, FL, United States, Apr. 7-11, 2002, PMSE-257. "Polyurethanes based on hydroformulated soybean oil." Guo, Andrew; Demydov, Dima; Zhang, Wei; Petrovic, Zoran S. Kansas Polymer Research Center, Pittsburg State University, Pittsburg, KS, USA. Publisher: American Chemical Society.
Journal of Molecular Catalysis A: Chemical (2002), 184(1-2), 65-71, "The hydroformylation of vegetable oils and model compounds by ligand modified rhodium catalysis." Kandanarachchi, Pramod; Guo, Andrew; Petrovic, Zoran. Kansas Polymer Research Center, Pittsburg State University, Pittsburg, KS, USA. Publisher: Elsevier Science B.V.
Journal of Polymers and the Environment (2002), 10(1/2), 49-52. "Polyols and Polyurethanes from Hydroformylation of Soybean Oil." Guo, Andrew; Demydov, Dima; Zhang, Wei; Petrovic, Zoran S. Kansas Polymer Research Center, Business and Technology Institute, Pittsburg, KS, USA. Publisher: Kluwer Academic/Plenum Publishers.
Journal of the Americal Oil Chemists' Society (1974), 51(5), 224-8 "Ethylene and dimethyl acetals from hydroformylated linseed, soybean, and safflower methyl esters as plasticizers for poly(vinyl chloride)." Awl, R.A.; Frankel, E.N.; Pryde, E.H.; Riser, G.R. North.Reg. Res. Lab., Agric. Res. Serv., Peoria, IL, USA.
Journal of the American Oil Chemists' Society (1977), 54(7), 276-8 "Recovery of solubilized rhodium from hydroformylated vegetable oils and their methyl esters." Dufek, E.J.; List, G.R.
Journal of the American Oil Chemists' Society (2002), 79(12), 1221-1225. "Kinetics of the hydroformylation of soybean oil by ligand-modified homogeneous rhodium catalysis." Kandanarachchi, Pramod; Guo, Andrew; Demydov, Dmytro; Petrovic, Zoran. Kansas Polymer Research Center, Pittsburg State University, Pittsburg, KS, USA. Publisher: AOCS Press. Journal of the American Oil Chemists' Society (1969), 46(3), 133-8 "Hydroformylation of unsaturated fatty esters." Frankel, Edwin N.; Metlin, S.; Rohwedder, William K.; Wender, Irving. Northern Reg. Res. Lab., Peoria, IL, USA.
Journal of the American Oil Chemists' Society (1974), 51(8), 331-4 "Rigid urethane foams from hydroxymethylated castor oik, safflower, oleic safflower oil, and polyol esters of castor acids." Lyon, C.K.; Garrett, V.H.; Frankel, E.N. WRRL, Berkley, CA, USA.

(Continued)

*Primary Examiner* — Sikarl Witherspoon (57) ABSTRACT

An extraction process for a non-aqueous hydroformylation product composition to separate an aldehyde product and to recover a hydroformylation catalyst. The process involves mixing a non-aqueous hydroformylation product composition containing a mixture of formyl-substituted fatty acid triglyceride esters derived from hydroformylating a seed oil, a transition metal-organophosphine ligand wherein the organophosphine is ionically-charged, optionally free ionically-charged organophosphine ligand, and a polar organic solubilizing agent with water and an extraction solvent having low water solubility to recover an organic phase containing the mixture of formyl-substituted fatty acid triglycerides and the low solubility extraction solvent and an aqueous phase containing the transition metal-organophosphine ligand, optional free ligand, the organic solubilizing agent, and water. Optionally, the low solubility extraction solvent can be prepared in situ in the hydroformylation step.

20 Claims, 1 Drawing Sheet

OTHER PUBLICATIONS

Journal of the American Oil Chemists' Society (1976), 53(5), 198-203 "Some esters of mono-, di-, and tricarboxystearic acid as plasticizers: preparation and evaluation." Dufek, E.J.; Thomas, F.L.; Frankel, E.N.; Riser, G.R. North. Res. Cent., ARS, Peoria, IL, USA.

Journal of the American Oil Chemists' Society (1977), 54(7), 271-5 "Analysis of hydroformylated vegetable oils and their methyl esters for rhodium." Dufek, E.J.; List, G.R. NRRC, ARS, Peoria, IL, USA.

*Journal of the Chemical Society*, pp. 276-288 (1958).

*Kirk-Othmer Encyclopedia of Chemical Technology*, vol. 10, $5^{th}$ edition, John Wiley & Sons Inc., "Fats and Fatty Oils," pp. 801-836, Feb. 2005.

*Organic Phosphorus Compounds*, vol. 1, by G.M. Kosolapoff and L. Maier, pp. 41-42 (1972), Wiley—Interscience.

\* cited by examiner

US 8,134,031 B2

EXTRACTION PROCESS FOR ALDEHYDE PRODUCT SEPARATION AND CATALYST RECOVERY

CROSS-REFERENCE TO RELATED APPLICATION

This application claims the benefit of U.S. provisional patent application 60/934,391, filed Jun. 13, 2007.

BACKGROUND OF THE INVENTION

In one aspect, this invention pertains to an extraction process for a hydroformylation product composition for the purpose of separating therefrom aldehyde products and for recovering a hydroformylation catalyst. In another aspect, this invention pertains to an integrated process of hydroformylating a seed oil in its native triglyceride form in the presence of a hydroformylation catalyst to produce a hydroformylation product composition, and thereafter of extracting the hydroformylation product composition for the purpose of separating therefrom aldehyde products and recovering a hydroformylation catalyst.

Seed oils comprise mixtures of triglyceride esters of mono-, di-, and tri-olefinically unsaturated fatty acids. The prior art describes hydroformylating a mono-olefinically-unsaturated fatty acid ester of a lower alkanol, such as a $C_{1-8}$ alkanol, with carbon monoxide and hydrogen (e.g., synthesis gas or syngas) in the presence of a rhodium-organophosphorus ligand complex catalyst and, optionally, free organophosphorus ligand to produce a mono-aldehyde product having one formyl substituent attached to the fatty acid chain ("monoformyl-substituted fatty acid ester"). When the reactant olefin is a di-unsaturated or tri-unsaturated fatty acid ester of a $C_{1-8}$ alkanol, hydroformylation may occur at each olefinic unsaturation to yield corresponding dialdehyde ("diformyl-substituted") and trialdehyde ("triformyl-substituted") products. Hydroformylating a mixture of mono-, di-, and tri-unsaturated fatty acid esters of $C_{1-8}$ alkanols, such as those derived from the transesterification of a seed oil with a lower alkanol, produces the corresponding aldehyde product comprising a mixture of monoformyl, diformyl, and triformyl-substituted fatty acid esters. As an unavoidable side reaction, a portion of the poly-unsaturated (di- and tri-unsaturated) fatty acid esters, which initially exist typically in unconjugated form, may isomerize to one or more conjugated poly-unsaturated fatty acid esters.

Mixtures of monoformyl, diformyl, and triformyl-substituted fatty acid esters can be derivatized via hydrogenation or hydroamination to yield corresponding alcohol, amine, or aminoalcohol derivatives, which can be condensed to form oligomeric polyols, polyamines, or polyamino alcohols. The latter poly-functional compounds find utility in the manufacture of industrially useful polymers, most notably, polyurethanes.

With regard to the aforementioned hydroformylation and hydrogenation processes, reference is made to International Patent Application Publications WO 2004-A1-096744 and WO 2004-A1-096882. Typically, said hydroformylation processes are conducted in a non-aqueous reaction medium, because fatty acid esters possess little, if any, solubility in water. Typically, such hydroformylation processes employ a transition metal-organophosphorus ligand complex catalyst and, optionally, free ligand. The transition metal is preferably rhodium; the ligand preferably comprises an ionically-charged organophosphine compound. Significantly, the one or more olefinically-unsaturated fatty acid esters comprise lower alkanol esters, specifically, $C_{1-8}$ alkanol esters. Methyl esters are preferably employed. A non-aqueous hydroformylation product composition derived therefrom can be extracted to separate the one or more aldehyde products and to recover a liquid stream containing the hydroformylation catalyst and optional free ligand for recycle to the hydroformylation process. U.S. Pat. No. 5,180,854 and WO-A1-2007/133379 (International Patent Application PCT/US2007/09452 of Dow Global Technologies Inc.), for example, disclose such extraction methods, which typically involve adding water, and optionally a nonpolar extraction solvent, to the non-aqueous hydroformylation product composition and by phase separation obtaining a nonpolar phase comprising one or more aldehyde products, optionally, one or more unconverted unsaturated fatty acid esters, and optionally, nonpolar solvent, and a polar phase comprising the transition metal-organophosphine ligand complex wherein the ligand is ionically-charged, optionally free ionically-charged organophosphine ligand, the organic solubilizing agent, and water. Additionally, WO 2007/133379 discloses that losses of transition metal, particularly rhodium, into the nonpolar phase can be reduced if certain pressure conditions are applied during the hydroformylation and extraction steps.

Seed oils in their native triglyceride form are more difficult to process, because molecular weights of fatty acid esters of glycerol (a trihydric alcohol) are significantly higher than those of $C_{1-8}$ alkanols. Moreover, hydroformylation products derived from native seed oils comprise molecules having a wide range of formyl functional groups (0 to 9), which imparts a greater range of physical properties, such as solubility in nonpolar organic solvents as well as water, which in turn makes it more difficult to separate the products from the hydroformylation catalyst. As a consequence, industrial processes using seed oils often begin with a preliminary step of transesterifying the seed oil triglycerides with a lower alkanol to obtain fatty acid esters of relatively lower molecular weights, such as methyl esters.

Hydroformylation processes of fatty acid esters would be more advantageously exploited if seed oils in their native triglyceride form absent transesterification to lower alkanol esters could be employed. Commercialization, however, of the hydroformylation of native seed oils will depend upon an efficient and clean extraction method to separate the resulting aldehyde products from the hydroformylation product composition. Moreover, commercialization also depends upon efficient recovery of the hydroformylation catalyst. Even a small loss of transition metal, such as rhodium, into the aldehyde products necessitates supplying make-up metal to the hydroformylation process; else the catalyst is continuously depleted. Since rhodium is a favored transition metal in hydroformylation processes, but one of the most expensive, loss of rhodium in particular is unacceptable. Furthermore, transition metal residue in the aldehyde products can lead to downstream problems; for example, rhodium is known to interfere with hydrogenation of the aldehyde products.

Up until the present invention, the extraction of aldehyde products derived from the hydroformylation of seed oils in their native triglyceride form has been unsuccessful. Separation has not been clean and efficient, and transition metal, particularly rhodium, remaining in the aldehyde products has been unacceptably high, exceeding 20 parts per million (ppm) based upon the weight of the aldehyde product composition. Significantly, seed oils provide sustainable chemical feedstocks that in specialized instances can replace conventional petroleum-based feedstocks in the manufacture of industrially useful chemicals. In order to advance the replacement of petroleum-based feedstocks with seed oil-based feedstocks, the art would benefit from having available an extraction method for separating aldehyde products derived from the hydroformylation of seed oils in their native triglyceride form and for recovering the hydroformylation catalyst.

SUMMARY OF THE INVENTION

In one aspect, the invention disclosed herein provides for a novel extraction process for a hydroformylation product composition derived from hydroformylation of a seed oil in its native triglyceride form to separate therefrom an aldehyde product and to recover a hydroformylation catalyst. The novel extraction process comprises mixing a non-aqueous hydroformylation product composition comprising a mixture of formyl-substituted fatty acid triglyceride esters, a transition metal-organophosphine ligand complex wherein the organophosphine ligand is ionically charged, optionally free ionically-charged organophosphine ligand, and a polar organic solubilizing agent for said complex and said free ligand with water and an extraction solvent having low water solubility, under conditions sufficient to obtain by one or more stages of phase separation an organic phase comprising the mixture of formyl-substituted fatty acid triglyceride esters and the extraction solvent having low water solubility and an aqueous phase comprising the transition metal-organophosphine ligand complex wherein the ligand is ionically-charged, optionally free ionically-charged organophosphine ligand, the polar organic solubilizing agent, and water.

In another aspect, there is provided herein an integrated process of hydroformylating a seed oil in its native triglyceride form and extracting a hydroformylation product composition derived therefrom to separate an aldehyde product and to recover a hydroformylation catalyst. The integrated process comprises:

(a) hydroformylating a seed oil comprising a mixture of olefinically-unsaturated fatty acid triglyceride esters with carbon monoxide and hydrogen in the presence of a transition metal-organophosphine ligand complex catalyst wherein the organophosphine ligand is ionically-charged, optionally free ionically-charged organophosphine ligand, and a polar organic solubilizing agent for said complex and said optional free ligand, in a hydroformylation reactor under reaction conditions sufficient to obtain a non-aqueous hydroformylation product composition comprising a mixture of formyl-substituted fatty acid triglyceride esters, the transition metal-organophosphine ligand complex wherein the ligand is ionically-charged, optionally free ionically-charged organophosphine ligand, and the polar organic solubilizing agent for said complex and said optional free ligand; and thereafter (b) mixing the non-aqueous hydroformylation product composition with water and an extraction solvent having low water solubility, under conditions sufficient to obtain by one or more stages of phase separation an organic phase comprising the mixture of formyl-substituted fatty acid triglyceride esters and the extraction solvent having low water solubility, and an aqueous phase comprising the transition metal-organophosphine ligand complex wherein the ligand is ionically-charged, optionally the free ionically-charged organophosphine ligand, the polar organic solubilizing agent, and water.

In yet another aspect there is provided herein a second integrated process of hydroformylating a seed oil in its native triglyceride form and extracting a hydroformylation product composition derived therefrom to separate an aldehyde product and to recover a hydroformylation catalyst. The process comprises:

(a) hydroformylating a seed oil comprising a mixture of olefinically unsaturated fatty acid triglyceride esters and simultaneously hydroformylating therewith a $C_{3-6}$ olefin with carbon monoxide and hydrogen in the presence of a transition metal-organophosphine ligand complex catalyst wherein the organophosphine ligand is ionically-charged, optionally free ionically-charged organophosphine ligand, and a polar organic solubilizing agent for said complex and said optional free ligand, in a hydroformylation reactor under reaction conditions sufficient to obtain a non-aqueous hydroformylation product composition comprising a mixture of formyl-substituted fatty acid triglyceride esters, one or more $C_{4-7}$ aldehydes capable of serving as an extraction solvent having low water solubility, the transition metal-organophosphine ligand complex wherein the ligand is ionically-charged, optionally free ionically-charged organophosphine ligand, and the polar organic solubilizing agent for said complex and said optional free ligand; and thereafter (b) mixing the non-aqueous hydroformylation product composition with water, under conditions sufficient to obtain by one or more stages of phase separation an organic phase comprising the mixture of formyl-substituted fatty acid triglyceride esters and the one or more $C_{4-7}$ aldehydes serving as the extraction solvent having low water solubility and an aqueous phase comprising the transition metal-organophosphine ligand complex wherein the ligand is ionically-charged, optionally the free ionically-charged organophosphine ligand, the polar organic solubilizing agent, and water.

In another aspect, after the extraction step, this invention further comprises (c) removing water from the aqueous phase and recycling a resulting non-aqueous polar phase comprising the transition metal-organophosphine ligand complex wherein the ligand is ionically-charged, optionally free ionically-charged organophosphine ligand, and the polar organic solubilizing agent back to the hydroformylation step (a).

In yet another aspect, this invention provides for an aldehyde composition comprising a mixture of formyl-substituted fatty acid triglyceride esters, the composition being prepared by the combined hydroformylation and extraction process steps described hereinabove.

The extraction process of this invention is usefully applied to separating an aldehyde product comprising a mixture of formyl-substituted fatty acid triglyceride esters derived from the hydroformylation of a seed oil in its native triglyceride form from a hydroformylation product composition and concurrently to recovering a hydroformylation catalyst comprising a transition metal and an ionically-charged organophosphine ligand. Surprisingly, the separation of the mixture of aldehyde products is clean and efficient, despite their relatively high molecular weight as triglyceride esters and their broad distribution of polarities due to the possible number of formyl groups on each triglyceride ester molecule. More surprisingly, this invention provides for recovery of transition metal used in the hydroformylation catalyst, particularly rhodium, with a high degree of efficiency, as defined hereinafter. Purer aldehyde products minimize losses of expensive transition metal and adverse effects of residual metal in downstream processing of the aldehyde products.

DETAILED DESCRIPTION OF THE INVENTION

References to the Periodic Table of the Elements herein shall refer to the Periodic Table of the Elements, published in *Nomenclature of Inorganic Chemistry: IUPAC Recommendations* 2005, Royal Society of Chemistry, 2005, ed. N. G. Connelly and T. Damhus. Also, any references to a Group or Groups of elements shall be to the Group or Groups reflected in this Periodic Table of the Elements using the IUPAC system for numbering groups.

All percentages, preferred amounts or measurements, ranges and endpoints thereof herein are inclusive, that is, "less than about 10" includes about 10. "At least" is equivalent to "greater than or equal to," and "at most" is, thus, equivalent "to less than or equal to." Numbers herein have no more precision than stated. Thus, "115" includes at least from 114.6 to 115.5. All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus a range that has an advantageous lower limit combined with a most preferred upper limit is preferred for the practice of this invention. The term "advantageously" is used to denote a degree of preference more than required, but less than is denoted by the term "preferably."

Except in the examples, or where otherwise indicated, all numbers expressing quantities, percentages, properties, functionalities and so forth in the specification are to be understood as being modified in all instances by the term "about." Unless stated otherwise, when an element, material, or step capable of causing undesirable effects is present in amounts or in a form such that it does not cause the effect to an unacceptable degree, that element, material, or step is considered substantially absent for the practice of this invention. Those skilled in the art recognize that acceptable limits vary with equipment, conditions, applications, and other variables, but are determinable without undue experimentation in each situation where they are applicable. In some instances, variation or deviation in one parameter is acceptable to achieve another desirable end.

The term "comprising", is synonymous with "including," "containing," or "characterized by," is inclusive or open-ended, and does not exclude additional, unrecited elements, material, or steps. The term "consisting essentially of" indicates that in addition to specified elements, materials, or steps; unrecited elements, materials or steps are optionally present in amounts that do not unacceptably materially affect at least one basic and novel characteristic of the subject matter. The term "consisting of" indicates that only stated elements, materials or steps are present except that unrecited elements, materials or steps are optionally present to an extent that has no appreciable effect, or are substantially absent.

The subject invention described herein provides for a novel extraction process for a hydroformylation product composition derived from hydroformylation of a seed oil in its native triglyceride form to separate therefrom an aldehyde product and to recover a hydroformylation catalyst. The novel extraction process comprises mixing a non-aqueous hydroformylation product composition comprising a mixture of formyl-substituted fatty acid triglyceride esters, a transition metal-organophosphine ligand complex wherein the organophosphine ligand is ionically charged, optionally free ionically-charged organophosphine ligand, and a polar organic solubilizing agent for said complex and said free ligand with water and an extraction solvent having low water solubility, under conditions sufficient to obtain by one or more stages of phase separation an organic phase comprising the mixture of formyl-substituted fatty acid triglyceride esters and the extraction solvent having low water solubility and an aqueous phase comprising the transition metal-organophosphine ligand complex wherein the ligand is ionically-charged, optionally free ionically-charged organophosphine ligand, the polar organic solubilizing agent, and water.

In another aspect, there is provided herein an integrated process of hydroformylating a seed oil in its native triglyceride form and extracting a hydroformylation product composition derived therefrom to separate an aldehyde product and to recover a hydroformylation catalyst. The integrated process comprises:

(a) hydroformylating a seed oil comprising a mixture of olefinically-unsaturated fatty acid triglyceride esters with carbon monoxide and hydrogen in the presence of a transition metal-organophosphine ligand complex catalyst wherein the organophosphine ligand is ionically-charged, optionally free ionically-charged organophosphine ligand, and a polar organic solubilizing agent for said complex and said optional free ligand, in a hydroformylation reactor under reaction conditions sufficient to obtain a non-aqueous hydroformylation product composition comprising a mixture of formyl-substituted fatty acid triglyceride esters, the transition metal-organophosphine ligand complex wherein the ligand is ionically-charged, optionally free ionically-charged organophosphine ligand, and the polar organic solubilizing agent for said complex and said optional free ligand; and thereafter (b) mixing the non-aqueous hydroformylation product composition with water and an extraction solvent having low water solubility, under conditions sufficient to obtain by one or more stages of phase separation an organic phase comprising the mixture of formyl-substituted fatty acid triglyceride esters and the extraction solvent having low water solubility, and an aqueous phase comprising the transition metal-organophosphine ligand complex wherein the ligand is ionically-charged, optionally the free ionically-charged organophosphine ligand, the polar organic solubilizing agent, and water.

In yet another aspect, there is provided herein a second integrated process of hydroformylating a seed oil in its native triglyceride form and extracting a hydroformylation product composition derived therefrom to separate an aldehyde product and to recover a hydroformylation catalyst. The process comprises:

(a) hydroformylating a seed oil comprising a mixture of olefinically unsaturated fatty acid triglyceride esters and simultaneously hydroformylating a $C_{3-6}$ olefin with carbon monoxide and hydrogen in the presence of transition metal-organophosphine ligand complex catalyst wherein the organophosphine ligand is ionically-charged, optionally free ionically-charged organophosphine ligand, and a polar organic solubilizing agent for said complex and said optional free ligand, in a hydroformylation reactor under reaction conditions sufficient to obtain a non-aqueous hydroformylation product composition comprising a mixture of formyl-substituted fatty acid triglyceride esters, one or more $C_{4-7}$ aldehydes capable of serving as an extraction solvent having low water solubility, the transition metal-organophosphine ligand complex wherein the ligand is ionically-charged, optionally free ionically-charged organophosphine ligand, and the polar organic solubilizing agent for said complex and said optional free ligand; and thereafter (b) mixing the non-aqueous hydroformylation product composition with water under conditions sufficient to obtain by one or more stages of phase separation an organic phase comprising the mixture of formyl-substituted fatty acid triglyceride esters and the one or more $C_{4-7}$ aldehydes serving as the extraction solvent having low water solubility and an aqueous phase comprising the transition metal-organophosphine ligand complex wherein the ligand is ionically-charged, optionally the free ionically-charged organophosphine ligand, the polar organic solubilizing agent, and water.

In another aspect, after the extraction step, this invention further comprises (c) removing water from the aqueous phase and recycling a resulting polar non-aqueous phase comprising the transition metal-organophosphine ligand complex wherein the ligand is ionically-charged, optionally free ionically-charged organophosphine ligand, and the polar organic solubilizing agent back to the hydroformylation step (a).

In a preferred embodiment, the extraction solvent comprises a single polar compound, a mixture of polar compounds, or a mixture of one or more polar compounds and one or more nonpolar compounds, said extraction solvent being a liquid under extraction conditions and having a solubility in water ranging from about 0.10 grams to about 7 grams per 100 grams water. In a more preferred embodiment, the extraction solvent comprises a single polar compound or a mixture of polar compounds, liquid under extraction conditions and having a solubility in water ranging from about 0.10 to about 1.8 grams per 100 grams water. In another preferred embodiment, the extraction solvent comprises a mixture of one or more polar compounds and one or more nonpolar compounds, the mixture being a liquid under extraction conditions and having a solubility in water ranging from greater than about 1.8 to less than about 7 grams per 100 grams water.

In yet another aspect, this invention provides for an aldehyde composition comprising a mixture of formyl-substituted fatty acid triglyceride esters, the composition being prepared by the combined hydroformylation and extraction process steps described hereinabove.

As seen from the above discussion, this invention is directed in part to separating aldehyde products from a non-aqueous hydroformylation product composition via phase separation. The term "non-aqueous hydroformylation product composition," as employed herein, means a non-aqueous composition comprising a mixture of aldehyde products, specifically, a mixture of formyl-substituted fatty acid triglyceride esters derived from hydroformylation of a seed oil (or a mixture of seed oils) in its native triglyceride form, a metal-organophosphine ligand complex wherein the ligand is ionically-charged, optionally free ionically-charged organophosphine ligand, and a polar organic solubilizing agent for said complex and said free ligand. Optionally, the "non-aqueous hydroformylation product composition" may also contain an extraction solvent having low water solubility (hereinafter referred to as the "low solubility extraction solvent") which may be produced in situ during hydroformylation as described hereinafter.

For the purposes of this invention, the term "non-aqueous," as employed herein with regard to the hydroformylation product composition, means that the hydroformylation product composition fed to the extraction stage is free or essentially free of water, which means that any water, if present at all, is not present in an amount sufficient to cause the hydroformylation product composition to be considered as encompassing a separate aqueous or water phase or layer in addition to an organic phase. In the extraction stage water is deliberately added to the hydroformylation product composition, after which addition the composition is no longer considered to be non-aqueous.

The term "aldehyde," as used herein, is given its well-known meaning in the field of organic chemistry. Specifically, since the hydroformylation employs carbon monoxide and hydrogen, reference to product "aldehyde" is synonymous with the presence of a "formyl" substituent (—CH═O), herein specifically attached to a fatty acid chain, because the feedstock to the hydroformylation comprises a mixture of olefinically-unsaturated fatty acid triglycerides.

The term "ligand" generally refers to any neutral molecule or charged ion that is bound to or complexed with a metal of a metal-ligand complex. In this invention, the metal is a transition metal, preferably, rhodium. With reference to the ligand, the term "ionically-charged" means that the ligand contains at least one negatively-charged anionic substituent; each such substituent being counter-balanced by a positively-charged cation. As a preferred example, the ionically-charged substituent may be a monovalent anionic sulfonyl group attached to any element of the ligand and counter-balanced by a monovalent cation, such as, a sodium ion.

The term "free organophosphine ligand," as used herein, means that the organophosphine ligand is not complexed with, tied to, or bound to a metal atom in a transition metal-ligand complex.

The term "organophosphine" as used herein refers to a tri(organo)phosphine compound wherein at least one trivalent phosphorus atom is present and is bonded to three hydrocarbyl or substituted hydrocarbyl groups, as described in detail hereinafter.

The non-aqueous hydroformylation product composition employable herein can and normally will contain additional components such as those that have either been deliberately employed in the non-aqueous hydroformylation process or those formed in situ during the hydroformylation process. Examples of such additional components include carbon monoxide and hydrogen gases, saturated fatty acid triglyceride esters originating in the seed oil (i.e., wherein each carbon in the fatty acid chain is bonded to four other atoms), in-situ formed products, such as, saturated fatty acid triglycerides arising from hydrogenation of unsaturated bonds and high boiling liquid aldehyde condensation by-products, as well as other inert co-solvent materials or hydrocarbon additives, as may be employed. The hydroformylation product composition may also contain one or more unconverted fatty acid triglycerides having mono or poly-olefinic unsaturation. Any poly-olefinically unsaturated fatty acid chain may be in non-conjugated form, as typically found in the native seed oil, or conjugated form as may arise from isomerization of unconjugated carbon-carbon double bonds under hydroformylation process conditions. As used herein, the term "conjugated" means that said olefinically-unsaturated fatty acid ester contains at least two carbon-carbon double bonds, C═C, that are separated by only one carbon-carbon single bond (C—C). In contrast, the term "unconjugated" refers to said olefinically-unsaturated fatty acid ester containing at least two carbon-carbon double bonds (C═C) that are separated by two or more carbon-carbon single bonds (C—C).

The aldehyde product contained in the non-aqueous hydroformylation product composition that is separated therefrom by the extraction process of this invention comprises a mixture of formyl-substituted fatty acid triglycerides (aldehyde esters), each fatty acid chain typically comprising from about 12 to about 25 carbon atoms. Consequently, each aldehyde product typically comprises from about 36 to about 84 carbon atoms arising from fatty acid chains (not counting the carbon atoms in the glycerol portion of the aldehyde product). Such mixtures are obtained upon hydroformylating a seed oil containing a mixture of triglycerides esters of mono-, di-, and/or tri-olefinically-unsaturated fatty acids, each fatty acid typically comprising from about 12 to about 25 carbon atoms. Formyl substitution via hydroformylation may occur at any of the carbon-carbon double bonds; and thus, any fatty acid triglyceride in the seed oil may contain from 1 to 9 formyl substituents depending upon the number of carbon-carbon double bonds present.

The seed oils from which the aldehyde product composition is derived can be selected from any natural or genetically modified (GMO) plant or vegetable oil, non-limiting examples of which include castor, soybean, olive, peanut, rapeseed, corn, sesame, cottonseed, canola, safflower, sunflower, and high oleic oils, as well as genetically-modified variations of the aforementioned oils, and mixtures thereof. Preferably, the seed oil is selected from soybean (natural and GMO), castor, sunflower, and canola oils, particular high-oleic embodiments thereof, as well as mixtures of any of the aforementioned oils. The term "high-oleic" as used herein means that the oleic acid content of the oil is greater than about 70 weight percent, based on the total weight of the free fatty acids from the seed oil. Seed oils and their constituent fatty acid components are described in detail in *Kirk-Othmer Encyclopedia of Chemical Technology*, Volume 10, 5$^{th}$ edition, John Wiley & Sons Inc., "Fats and Fatty Oils," pp. 801-836, the disclosure of which is incorporated herein by reference.

The seed oil triglycerides from which the hydroformylation product composition is derived preferably comprise greater than about 65 percent, preferably, greater than about 70 percent, and more preferably, greater than about 80 percent unsaturated fatty acids, by weight of the total fatty acids, the balance to 100 percent being typically saturated fatty acids. More preferably, the seed oil triglycerides comprise from greater than about 10 to less than about 95 percent mono-unsaturated fatty acids by weight; from greater than about 4 to less than about 60 percent di-unsaturated fatty acids by weight; and from greater than about 1 to less than about 70 percent tri-unsaturated fatty acids, by weight.

An advantage of the present invention is that the seed oil is hydroformylated in its native form as a mixture of triglyceride esters. The conventional step of transesterifying the native seed oil with a lower alkanol, namely, a $C_{1-8}$ alkanol, is not conducted and beneficially avoided. The native seed oil may be subjected, however, to other types of conventional pretreatment processing prior to use in the hydroformylation process of this invention. Some well-known conventional processing methods include dehulling, defoaming, decolorizing, and/or bleaching processes, known to those of skill in the art.

Non-aqueous hydroformylation process conditions capable of converting a native seed oil or mixture thereof to the non-aqueous hydroformylation product composition useful in this invention vary widely and are known in the art. For instance, generally, it is preferred to employ the operational features taught in U.S. Pat. No. 4,731,486, U.S. Pat. No. 4,633,021, U.S. Pat. No. 4,731,486, WO 2004/096744 and WO 2006/012344, the disclosures of which are incorporated herein by reference. In accordance with the aforementioned references, the reaction conditions for effecting such non-aqueous hydroformylation processes advantageously comprise a reaction temperature greater than about 50° C., preferably, greater than about 60° C., and more preferably, greater than about 65° C. The reaction temperature advantageously is less than about 150° C., preferably, less than about 130° C., and more preferably, less than about 110° C. For such hydroformylation processes, advantageously, the total reactor pressure may range from about 100 psia (689 kPa) to about 5,000 psia (34.5 MPa). For the purposes of this invention, preferably, the total reactor pressure is greater than about 200 psia (689 kPa), and more preferably, greater than about 300 psia (1378 kPa). Preferably, the total reactor pressure is less than about 1000 psia (4,137 kPa), and more preferably, less than about 800 psia (3103 kPa). Carbon monoxide partial pressure of the non-aqueous hydroformylation process advantageously is greater than about 50 psia (345 kPa), and preferably, greater than about 125 psia (862 kPa). The carbon monoxide partial pressure of the non-aqueous hydroformylation process advantageously is less than about 500 psia (3,448 kPa), and preferably, less than about 400 psia (2,069 kPa). Hydrogen partial pressure of the non-aqueous hydroformylation process advantageously is greater than about 50 psia (345 kPa), and preferably, greater than about 100 psia (689 kPa). The hydrogen partial pressure of the non-aqueous hydroformylation process advantageously is less than about 500 psia (3,448 kPa), and preferably, less than about 400 psia (2,069 kPa). Advantageously, a $H_2$:CO molar ratio of gaseous hydrogen to carbon monoxide can range from about 1:5 to 5:1 or higher, the more preferred hydrogen to carbon monoxide molar ratio being about 1:1.

The hydroformylation process is conducted in the presence of transition metal-organophosphine ligand complex catalyst wherein the ligand is ionically-charged, and optionally, free ionically-charged organophosphine ligand, and a polar solubilizing agent for solubilizing the complex catalyst and optional free ligand in the non-aqueous hydroformylation reaction medium. Each of these components will be discussed in detail hereinafter. Moreover, while it is clear that the hydroformylation process can be conducted in a batch type process, a continuous process with a liquid catalyst recycle to the hydroformylation reactor is more desirable.

In an optional aspect of this invention, the hydroformylation can be conducted in the presence of a $C_{3-6}$ olefin, which under process conditions is converted to the corresponding $C_{4-7}$ aldehyde. The aldehyde thusly-produced is capable of functioning as an extraction solvent having low solubility in water, which notably is a required component of the subsequent extraction step. Further details are presented hereinafter. Non-limiting examples of suitable $C_{3-6}$ olefins include propene, butenes, butene-1 and butene-2 raffinates, pentenes, hexenes, and mixtures thereof. Preferably, the $C_{3-6}$ olefin is selected from readily available and inexpensive butene-1 and butene-2 raffinate streams obtainable from petroleum crackers and comprising mixtures of varying concentrations of butene-1, butene-2, isobutylene and butadiene.

The total amount of aldehyde products present in the non-aqueous hydroformylation product composition employable as a feed to one or more phase separation stages of the extraction step can range from about 10 to about 90 weight percent, based on the weight of the hydroformylation product composition. Preferably, the total amount of the aldehyde products present in the non-aqueous hydroformylation product composition employable as the feed to the one or more phase separation stages of the extraction step can range from about 20 to about 80 weight percent, based on the weight of the hydroformylation product composition.

The hydroformylation product composition comprises an ionically-charged organophosphine ligand which exists either bound to metal in a complex or unbound to metal (free).

Preferably, the organophosphine ligand consists essentially of a monosulfonated tertiary phosphine metal salt having the general formula:

wherein $R^1$ and $R^2$ each individually represent a radical containing from 1 to about 30 carbon atoms selected from the group consisting of alkyl, aryl, alkaryl, aralkyl and alicyclic radicals; wherein $R^3$ represents a divalent alkylene radical having from 2 to about 12, preferably 2 to about 5 carbon atoms, or a divalent 1,3-phenylene radical; wherein M represents a metal cation selected from the group consisting of alkali and alkaline earth metals; and wherein n has a value of 1 or 2 corresponding to the valence of the particular metal cation represented by M. As seen in the formula hereinabove, the sulfonate group is a negatively charged anion (−1), which for charge balance requires a positively charged cation. Hence, the skilled artisan understands the term "ionically-charged" to mean that the organophosphorus ligand contains a positively and negatively charged ion pair.

Illustrative radicals represented by the $R^1$ and $R^2$ in the above monosulfonated tertiary phosphine metal salt formula include monovalent hydrocarbon radicals containing from 1 to 30 carbon atoms, e.g., alkyl radicals including linear or branched, primary, secondary or tertiary alkyl radicals, such as methyl, ethyl, n-propyl, isopropyl, butyl, sec-butyl, t-butyl, t-butylethyl, t-butylpropyl, n-hexyl, amyl, sec-amyl, t-amyl, 2-ethylhexyl, n-octyl, iso-octyl, decyl, dodecyl, octadecyl, and eicosyl; aryl radicals, such as phenyl and naphthyl; aralkyl radicals, such as benzyl and phenylethyl; alkaryl radicals, such as tolyl and xylyl; and alicyclic radicals, such as cyclopentyl, cyclohexyl, cyclooctyl, and cyclohexylethyl. The aforementioned examples are not meant to be limiting in any way. Moreover, such monovalent hydrocarbon radicals can be substituted with any substituent that does not unduly adversely affect the desired results of this invention. Illustrative substituents that may be on the hydrocarbon radicals include for example silyl radicals such as —Si($R^9$)$_3$, amino radicals such as —N($R^9$)$_2$, acyl radicals such as —C(O)$R^9$, acyloxy radicals such as —OC(O)$R^9$, amido radicals such as —CON($R^9$)$_2$ and —N($R^9$)COR$^9$, sulfonyl radicals such as —SO$_2$R$^9$, alkoxy radicals such as —OR$^9$, thionyl radicals such as —SR$^9$, phosphonyl radicals such as —P(O)(R$^9$)$_2$, as well as, halogen, nitro, cyano, trifluoromethyl, and hydroxy radicals, wherein each $R^9$ individually represents the same or different substituted or unsubstituted monovalent hydrocarbon radical having the same meaning as defined for $R^1$ and $R^2$ above, provided that in amino substituents such as —N($R^9$)$_2$, each $R^9$ taken together can also represent a divalent bridging group that forms a heterocyclic radical with the nitrogen atom, and in amido substituents such as —C(O)N($R^9$)$_2$ and —N($R^9$)COR$^9$ each $R^9$ bonded to N can also be hydrogen. Of course, it should be understood that the $R^1$ and $R^2$ groups in a particular given metal salt ligand may be the same or different.

When $R^3$ in the above formula represents a divalent 1,3-phenylene radical, preferably the monovalent hydrocarbon radicals represented by $R^1$ and $R^2$ are selected from the group consisting of alkyl radicals having from $C_1$ to $C_{20}$ carbon atoms, aryl radicals having from $C_6$ to $C_{12}$ carbon atoms, and alicyclic radicals having from $C_5$ to $C_{12}$ carbon atoms. More preferably, the $R^1$ and $R^2$ groups are each individually a branched chain alkyl radical having from about 3 to about 9 carbon atoms (such as isopropyl, t-butyl, etc.), or a phenyl or a cyclohexyl radical. Most preferably, the $R^1$ and $R^2$ radicals in a given monosulfonated tertiary phosphine metal salt each individually represent a phenyl or cyclohexyl radical, especially cyclohexyl, when $R^3$ is a divalent 1,3-phenylene radical.

When $R^3$ in the above formula represents a divalent alkylene radical, preferably $R^1$ represents an aryl radical having from $C_6$ to $C_{12}$ carbon atoms or an alicyclic radical having from $C_5$ to $C_{12}$ carbon atoms and $R^2$ represents an alkyl radical having from $C_1$ to $C_{20}$ carbon atoms, an aryl radical having from $C_6$ to $C_{12}$ carbon atoms or an alicyclic radical having from $C_5$ to $C_{12}$ carbon atoms. More preferably $R^1$ is a phenyl or cyclohexyl radical and $R^2$ is a branched chain alkyl radical having from about 3 to about 9 carbon atoms (such as isopropyl, t-butyl, etc.), a phenyl or a cyclohexyl radical. Most preferably the $R^1$ and $R^2$ radicals in a given monosulfonated tertiary phosphine metal salt each individually represent a phenyl or a cyclohexyl radical, especially cyclohexyl when $R^3$ is a divalent alkylene radical having from about 2 to about 5 carbon atoms, especially 1,3-propylene or 1,4-butylene.

As noted, M in the monosulfonated tertiary phosphine metal salt ligand formula hereinabove represents a metal cation selected from the group consisting of alkali and alkaline earth metals. Illustrative alkali metals include lithium (Li+), sodium (Na+), potassium (K+), cesium (Cs+) and rubidium (Rb+), while illustrative alkaline earth metals include calcium (Ca++), barium (Ba++), magnesium (Mg++) and strontium (Sr++). Moreover as noted above by the definition of n, the metal salt ligand may contain one or two monosulfonated tertiary phosphine anions corresponding to the positive valence of the metal cation M (+1 or +2).

The more preferred class of monosulfonated tertiary phosphine metal salt ligands employable herein is that wherein $R^3$ represents a divalent 1,3-phenylene radical, which has the general formula:

wherein $R^1$, $R^2$, M and n may be the same as defined above, in contrast to those of the class wherein $R^3$ represents a divalent alkylene radical, which has the general formula:

wherein the divalent alkylene radical contains from 2 to 12 carbon atoms, and $R^1$, $R^2$, M and n are the same as defined above.

Illustrative preferred monosulfonated tertiary phosphine metal salt ligands include all of such compounds listed in U.S. Pat. No. 5,180,854, incorporated herein by reference. A most preferred ionic tertiary organophosphine ligand is dicyclohexylphenylphosphine monosulfonate metal salt. Such types of monosulfonated tertiary phosphine metal salt ligands employable in this invention and/or methods for their manufacture are well known, as seen, for example, in the procedures described in *Journal of the Chemical Society*, pp. 276-288 (1958), U.S. Pat. No. 4,483,802, U.S. Pat. No. 4,731,486, U.S. 5,180,854, and WO 2004/096744, all incorporated herein by reference. A preferred method of preparation is also disclosed in WO 2007/035540, incorporated herein by reference. Such ligands wherein $R^3$ in Formula (I) above is a divalent alkylene radical may be prepared, for example, by conventional nucleophilic substitution reactions such as taught in *Organic Phosphorus Compounds*, Vol. 1, by G. M. Kosolapoff and L. Maier, pp. 41-42 (1972), Wiley-Interscience.

Another component of the non-aqueous hydroformylation product composition is a transition metal-organophosphine ligand complex, which primarily corresponds to the transition metal-organophosphine ligand complex catalyst employed in the non-aqueous hydroformylation reaction process from which the hydroformylation product composition is derived. However, it is to be noted that the successful practice of this invention does not depend and is not predicated upon the exact structure of the transition metal-organophosphine complex species present in the hydroformylation product composition. Such species may be present in their mononuclear, dinuclear and/or higher nuclearity forms. Indeed the exact structure may not be known. Although it is not intended herein to be bound to any theory or mechanistic discourse, it is believed that the transition metal-organophosphine ligand complex may in its simplest form consist essentially of transition metal advantageously selected from Groups 8, 9, and 10 elements, preferably cobalt, rhodium, and palladium, more preferably rhodium, in complex combination with carbon monoxide and the ionically-charged organophosphine ligand. The composition of the transition metal-organo-phosphine ligand complex may also contain an additional inorganic or organic ligand, either neutral or anionic, and satisfying the coordination sites or nuclear charge of the metal. Hydrogen, for example, might also be bound to the metal. Advantageously, a transition metal concentration, for example, rhodium concentration, greater than about 10 parts per million (ppm), preferably, greater than about 50 ppm, more preferably, greater than about 100 ppm, is employed. Advantageously, a transition metal concentration less than about 1000 ppm, preferably, less than about 800 ppm, and more preferably, less than about 600 ppm is employed, by weight based on the weight of the hydroformylation reaction fluid.

The metal-organophosphine ligand complex may be prepared by methods known in the art. Since rhodium is a preferred metal, an example is provided to illustrate the preparation of rhodium-organophosphine ligand complex. For instance, preformed rhodium (hydrido) carbonyl monosulfonated tertiary phosphine metal salt ligand complexes may be prepared and introduced with a solubilizing agent, if necessary, into the reaction medium of the non-aqueous hydroformylation process. More commonly the rhodium-organophosphine ligand complex is derived from a metal catalyst precursor, such as rhodium dicarbonyl acetylacetonate, $Rh_2(CO)_3$, $Rh_4(CO)_{12}$, $Rh_6(CO)_{16}$, $Rh(NO_3)_3$, which can be introduced along with the ionic tertiary organophosphine ligand, and an added organic solubilizing agent for the in-situ formation of the active catalyst for the hydroformylation process.

The amount of transition metal-organophosphine ligand complex present in the non-aqueous hydroformylation product composition fed to the extraction step generally corresponds to the amount of corresponding complex present in the reaction medium of the hydroformylation process from which said hydroformylation product composition is derived. Generally, the amount of transition metal-organophosphine ligand complex present in the reaction medium of a given hydroformylation process is expressed in terms of the amount of transition metal present, such amounts of metal being noted hereinbefore. Accordingly, the amount of transition metal-organophosphine ligand complex present in the non-aqueous hydroformylation product ranges from greater than about 10 ppm, preferably, greater than about 50 ppm, and more preferably, greater than about 100 ppm, to less than about 1000 ppm, preferably, less than about 800 ppm, and more preferably, less than about 600 ppm, transition metal by weight, based on the weight of the hydroformylation product composition.

The amount of organophosphine ligand present in the non-aqueous hydroformylation product composition is similar to that amount of ligand present in the hydroformylation reaction medium from which the non-aqueous hydroformylation product composition is derived. Advantageously, the amount of organophosphine ligand in the non-aqueous hydroformylation product composition is greater than about 0.2 percent, and preferably, greater than about 0.5 percent, and more preferably, greater than about 1.0 percent, by weight, based on the weight of the non-aqueous hydroformylation product composition. Advantageously, the amount of organophosphine ligand in the non-aqueous hydroformylation product composition is less than about 4.0 percent, preferably, less than about 3.0 percent, and more preferably, less than about 2.5 percent, by weight, based on the weight of the non-aqueous hydroformylation product composition.

As noted above, the ionically-charged organophosphine ligands defined herein are employed in this invention as both the organophosphine ligand of the transition metal-ligand complex and as the free ligand present in the non-aqueous hydroformylation product composition. While the ionically-charged organophosphine ligand of the metal-ligand complex and the free ligand are normally identical, they can be different; and alternatively, mixtures of two or more ionically-charged organophosphine ligands can be employed, if desired. The amount of free organophosphine ligand present in the non-aqueous hydroformylation product composition fed to the extraction stage generally corresponds to the amount of corresponding free organophosphine ligand present in the reaction medium of the non-aqueous hydroformylation process. For instance, since the hydroformylation process can be carried out in any excess amount of free organophosphine ligand, such as, at least one mole of free monosulfonated tertiary phosphine metal salt ligand per mole of transition metal present in the reaction medium, the amount of free organophosphine ligand present in the non-aqueous hydroformylation product composition can also be any corresponding excess amount. In general, amounts of free organophosphine ligand of from about 1 to about 100, and preferably from about 2 to about 20 moles per mole of transition metal are suitable for both the hydroformylation process and the corresponding hydroformylation product composition.

The hydroformylation product composition employable in this invention also contains an organic solubilizing agent corresponding to that employed for solubilizing the transition metal-organophosphine ligand complex and free organophosphine ligand in the reaction medium of the hydroformylation process from which said hydroformylation product composition is derived. The organic solubilizing agent may be any polar organic liquid having a molecular weight of less than about 250 and a Hildebrand solubility value of about 10 or higher, and mixtures thereof. Illustrative and non-limiting examples of such polar compounds (along with their Hildebrand solubility parameters) include lower alcohols, e.g., methanol (12.9), ethanol (11.2), propanol (10.2), and isopropanol (10.2), as well as nitriles, e.g., benzonitrile (10.7), acetonitrile (11.8), and propionitrile; amides, e.g., dimethylformamide (11.5), dimethylacetamide, and N,N-dimethylpropionamide; pyrrolidones, e.g., N-methylpyrrolidone (14.8), N-methyl piperidone, 1,5-dimethyl pyrrolidone, 2-pyrrolidinone, 2-hydroxyethyl pyrrolidone, N-dodecyl pyrrolidone, N-ethyl pyrrolidone, N-cyclohexyl pyrrolidone, 1,2-di(pyrrolidone) ethane; glycols, e.g., ethylene glycol and propylene glycol; polyglycols, e.g., diethylene glycol, triethylene glycol, tetraethylene glycol, dipropylene glycol, and tripropylene glycol; sulfoxides, e.g., dimethyl sulfoxide (12.8); sulfones, e.g., dimethyl sulfone; and sulfolane. Hildebrand solubility values are an empirical measure of the relative polarity of an organic compound and are described, for example, in *Introduction to Modern-Liquid Chromatography*, by L. R. Snyder and J. J. Kirkland, pp. 215-218 (1974), a Wiley-Interscience publication, (John Wiley & Sons) and in The Solubility of Non-Electrolytes, J. H. Hildebrand and R. L. Scott, pp. 424-434, Dover Publications Inc., New York (1964). The preferred polar organic solubilizing agents are selected from amides, sulfoxides, sulfones, and mixtures thereof; the more preferred polar organic solubilizing agents being amides, for instance, N-methylpyrrolidone.

The aforementioned solubilizing agents can be employed individually or as mixtures of two or more different polar organic liquid compounds; and the total amount of such added polar organic solubilizing agent(s) present in the non-aqueous hydroformylation product composition generally corresponds to that amount employed in the reaction medium of the non-aqueous hydroformylation process from which the hydroformylation product composition is derived. Accordingly, the polar organic solubilizing agent(s) can be present in the non-aqueous hydroformylation product composition in an amount ranging from about 10 to about 55 weight percent, preferably, from about 20 to about 40 weight percent, based on the weight of the non-aqueous hydroformylation product composition.

An extraction solvent having low water solubility is required for the extraction step of this invention. The extraction solvent comprises a liquid under extraction conditions, and can comprise a single polar compound, a mixture of two or more polar compounds, or a mixture of one or more polar compounds and one or more nonpolar compounds. Advantageously, each compound in the extraction solvent has a normal boiling point greater than about 60° C., preferably, greater than about 65° C., but advantageously less than about 175° C., preferably, less than about 160° C., and more preferably, less than about 140° C. The words "low solubility in water" and "low solubility extraction solvent" mean that the solubility of the extraction solvent advantageously ranges from about 0.10 gram, preferably, from about 0.15 gram, to about 7 grams per 100 grams water (i.e., from about 1,000 parts per million by weight (ppmw), preferably, from about 1,500 ppmw to about 70,000 ppmw, based on the weight of the water). An individual compound in the extraction solvent can have a solubility less than 0.10 gram per 100 grams water or can reach up to a solubility as high as about 10 grams per 100 grams water (about 10,000 ppm, based on the weight of water); however, the extraction solvent composition should have a solubility in water between about 0.10 gram and about 7 grams per 100 grams water. When the extraction solvent comprises one or more polar solvents, the solubility in water of the single polar solvent or mixture thereof preferably ranges from about 0.10 gram to about 1.8 grams per 100 grams water. When a polar compound having a water solubility greater than about 1.8 grams per 100 grams water is used, a nonpolar compound is also required to achieve the desired fast and clean phase separation and to recover the catalyst. When the extraction solvent comprises one or more polar compounds and one or more nonpolar compounds, the solubility in water of the extraction solvent preferably ranges from greater than about 1.8 grams to about 7 grams per 100 grams water.

Polarity can be induced by various substituents on an organic molecule, for example, carbonyl, ether, amine, hydroxyl, and even alkyl substitution. Such substituents when asymmetrically positioned can induce a dipole moment in the molecule, rendering it "polar." Non-limiting examples of polar extraction solvents suitable for this invention include aldehydes, esters, ketones, tertiary amines, ethers and polar aromatic compounds, including polar aromatic hydrocarbons, provided that the compound is a liquid under extraction conditions and has the requisite low water solubility. Preferred examples of such compounds include $C_{4-7}$ aldehydes, such as butyraldehydes, pentaldehydes, hexyldehydes, heptaldehydes; $C_{4-8}$ esters, such as ethyl acetate, propyl acetate, ethyl propionate, methyl butyrate, ethyl butyrate, diethyl carbonate and analogous esters; $C_{4-8}$ ketones, such as, methyl propyl ketone (2-pentanone), diethyl ketone, and analogous ketones; $C_{4-8}$ ethers, such as, diisopropyl ether, methyl tert-butyl ether, dibutyl ether and analogous ethers; and $C_{7-12}$ polar aromatic solvents, such as ethylbenzene.

The nonpolar compound can be any nonpolar liquid hydrocarbon solvent containing from about 6 to about 10 carbon atoms. Generally, the nonpolar hydrocarbon solvent has a water solubility less than about 100 ppm by weight, based on the weight of water. Illustrative nonpolar hydrocarbons include, for example, alkanes containing from $C_6$ to $C_8$ carbon atoms having straight or branched chain structure, such as hexane (e.g., n-hexane, $H_2O$ solubility 13.3 parts per million by weight, ppmw, (25° C.)), heptane (n-heptane, $H_2O$ solubility 2.24 ppmw (25° C.)), and octane, olefinic compounds containing from $C_6$ to $C_8$ carbon atoms, including alpha-olefins containing from $C_6$ to $C_8$ carbon atoms, such as, hexenes (e.g., 1-hexene, $H_2O$ solubility 50 ppmw (25° C.)) and octenes (e.g., 1-octene, $H_2O$ solubility 4.10 ppm (25° C.)); cycloaliphatic compounds containing from $C_6$ to $C_8$ carbon atoms, such as, cyclohexane and cyclooctene; and aryl compounds having from $C_6$ to $C_8$ carbon atoms, including benzene. Of course, it is to be understood that such compounds may be substituted with any substituent that does not adversely affect the phase separation process of this invention. For example, illustrative substituted alkanes include fluorocarbons. Moreover, mixtures of two or more different nonpolar hydrocarbon solvents can be employed, if desired. Preferably, the nonpolar hydrocarbon solvent comprises a saturated straight chain alkane containing from $C_6$ to $C_8$ carbon atoms, most preferably, heptane.

The art discloses the water solubility and the normal boiling point of many polar and nonpolar organic compounds, as found for example in *Yaw's Handbook of Thermodynamic and Physical Properties of Chemical Compounds*, Knovel Publishers, 2003, and *Lange's Handbook of Chemistry* (15th *Edition*), McGraw-Hill, 1999, relevant sections of which are incorporated herein by reference. The solubility data are normally logged at 25° C. and are suitably applied to the extraction process herein, even if the extraction itself is conducted at a somewhat higher temperature. Non-limiting examples of organic compounds suitable for this invention and their solubility in water are listed in Table 1 hereinbelow.

TABLE 1

Water Solubility of Selected Organic Compounds[1,2]

| Organic Compound | Solubility in water (ppmw) |
|---|---|
| Cyclohexanone[3] | 93190 |
| Isobutyraldehyde[3] | 89000 |
| Butyraldehyde[3] | 83720 |
| Isobutanol[3] | 81000 |
| Butanol[3] | 74600 |
| Ethyl acetate[3] | 73720 |
| Methyl isopropyl ketone[3] | 60800 |
| 3-Methyl-2-butanol[3] | 56000 |
| Methyl propyl ketone[3] | 55360 |
| 3-Pentanol[3] | 52000 |
| Methyl tert-butyl ether[3] | 51260 |
| Methyl isopropenyl ketone[3] | 47000 |
| 2-Pentanol[3] | 45000 |
| Cyclohexanol[3] | 38160 |
| Diethyl ketone[3] | 34000 |
| 2-Methyl-1-butanol[3] | 30000 |
| Isopropyl acetate[3] | 29000 |
| 2-Methylbutanal[4] | 28212 |
| 3-Methylbutanal[4] | 27392 |
| 3-Methyl-1-butanol[3] | 27000 |
| 2-Methyl-3-pentanol[4] | 25882 |
| Ethyl isopropyl ketone[4] | 22865 |
| Propyl formate[3] | 22000 |
| Ethyl propanoate[3] | 22000 |
| 1-Pentanol[3] | 22000 |
| 4-Methyl-2-pentanone[3] | 19000 |
| Diethyl carbonate[3] | 18878 |
| Propyl acetate[4] | 16787 |
| 2-Hexanone[3] | 16400 |
| Methyl butyrate[3] | 15000 |
| 3-Hexanone[3] | 14700 |
| Pentanal[3] | 11700 |
| Diisopropyl ether[3] | 11250 |
| Ethyl butyrate[3] | 6168 |
| Hexanal[3] | 5644 |
| Dibutyl ether | 1850 |
| 1-Heptanal[3] | 1516 |
| 1-Hexene[3] | 50.0 |
| Hexane[3] | 13.3 |
| 1-Octene[3] | 4.10 |
| Heptane[3] | 2.24 |

[1]Solubility data are obtained from Yaw's Handbook of Thermodynamic and Physical Properties of Chemical Compounds, Knovel Publishers, 2003.
[2]Solubility data are measured at 25° C., with the exception of propyl formate and ethyl butyrate which are measured at 22° C.
[3]Experimental value
[4]Estimated value The extraction step is preferably directed to treating a non-aqueous hydroformylation product composition that has been directly obtained by removal of a corresponding liquid reaction medium from the hydroformylation reactor. The non-aqueous hydroformylation product composition can also encompass any non-aqueous hydroformylation product composition that is derived from the hydroformylation process and pre-treated in some manner prior to the extraction method of this invention. Of course, the pre-treated composition should be "non-aqueous," as defined herein, and should contain at least some amount of aldehyde product and rhodium-organophosphine ligand complex, optional free ligand, and solubilizing agent for the complex and free ligand. The amounts of each of said components in the pretreated non-aqueous composition can be the same or different as compared with those amounts of components present in the non-aqueous hydroformylation product composition obtained directly from the hydroformylation reactor. For instance, product compositions obtained directly from the reactor can be subjected to distillation to remove one or more volatile components, or can phase separate into a polar and nonpolar phase upon standing and/or when cooled to a lower temperature than the hydroformylation reaction temperature.

In one embodiment of this invention the extraction solvent is mixed with the hydroformylation product composition; but in another preferred embodiment the extraction solvent is synthesized in situ in the hydroformylation process prior to the extraction step. In this latter embodiment a $C_{3-6}$ olefin is added as a co-reactant to the seed oil feed to the hydroformylation reactor resulting in production of a $C_{4-7}$ aldehyde co-product along with the formyl-substituted fatty acid triglyceride ester products. The $C_{4-7}$ aldehyde possesses all of the requisite properties of the extraction solvent having low water solubility. Accordingly, the in situ production of the low solubility extraction solvent in the hydroformylation step avoids having to later mix the low solubility extraction solvent at the extraction stage.

The amounts of water and low solubility extraction solvent that are mixed with the hydroformylation product composition should be sufficient to provide an efficient and clean phase separation, preferably, such that the aldehyde-containing organic phase contains less than about 2.0 parts per million (ppm), more preferably, less than 1.0 ppm, and most preferably, less than 0.8 ppm (or 800 parts per billion, ppb) transition metal, based on the weight of the isolated aldehyde product. Preferably, the amounts of water and low solubility extraction solvent are sufficient to provide phase separation of greater than about 90 weight percent, preferably, greater than about 95 weight percent of the aldehyde product(s), based on the total weight of the aldehyde product(s) in the non-aqueous hydroformylation product composition. Preferably, the amounts of water and extraction solvent are sufficient to provide phase separation of greater than about 90 weight percent, preferably, greater than about 98 weight percent, of the free organophosphine ligand, calculated on the total weight of organophosphine ligand present in the hydroformylation product composition.

Preferably, the process of this invention comprises mixing the non-aqueous hydroformylation product composition with from about 2 to about 60 percent by weight, and more preferably from about 10 to about 30 percent by weight, of added water; and from about 20 to about 150 percent by weight, and more preferably, from about 50 to about 120 percent by weight, of extraction solvent having low water solubility; said amounts being based on the total weight of the non-aqueous hydroformylation product composition.

The volumes employed of low solubility extraction solvent and nonpolar hydrocarbon compound are beneficially given relative to the volume of the starting seed oil that is hydroformylated to form the hydroformylation product composition of this invention. This approach is rationalized on grounds that hydroformylation of the seed oil in the presence of solvent(s) and other reaction components transforms the seed oil molecules and its bulk density in a potentially complex manner. Accordingly, it is easier to estimate extraction volumes based on the volume of the starting seed oil. Accordingly, the volume ratio of low solubility extraction solvent to the starting seed oil advantageously is greater than about 0.3/1, preferably, greater than about 0.5/1, and more preferably, greater than about 0.7/1. The volume ratio of the low solubility extraction solvent to the starting seed oil advantageously is less than about 2.0/1, preferably, less than about 1.8/1, and more preferably, less than about 1.6/1.

The volume ratio of the nonpolar hydrocarbon (NPH) compound, if used, to the starting seed oil advantageously is greater than about 0.1/1, preferably, greater than about 0.2/1, and more preferably, greater than about 0.3/1. The volume ratio of the nonpolar hydrocarbon compound to the starting seed oil advantageously is less than about 1.6/1, preferably, less than about 1.3/1, and more preferably, less than about 1.0/1.

In a continuous integrated process, a portion of the liquid hydroformylation reaction medium can be continuously pumped from the reactor to a mixer to be thoroughly mixed with added water and low solubility extraction solvent, thereby resulting in the treated composition phase separating into two distinct liquid layers or phases. The mixing can be carried out in any conventional manner or fashion; for example, in a static mixer or a mixer with rotating parts, or a co-current or counter-current mixer, or using spray columns, provided that the equipment tolerates the pressure and temperature of the extraction. As used herein, the term "static mixer" refers to a vessel, preferably tubular in shape, with internal structures, such as perforated plates or baffles of any size or shape, which induce mixing of a liquid flowing through the vessel, without moving parts, such as, a blades rotated on a shaft. Static mixers are also referred to as "In-Line" mixers. A thorough mixing of the liquids is desired. Generally, it is preferred to add the water and low solubility extraction solvent (where such extraction solvent is not already synthesized in situ in the hydroformylation step) to the non-aqueous hydroformylation product composition and thoroughly mix in a static mixer, and then feed the resulting composition to a conventional decanter vessel for settling of organic and aqueous liquid phases. If the mixing produces a fine liquid emulsion (intimately mixed small liquid droplets), then the resulting composition can be sent to a coalescer prior to the decanter vessel to obtain larger liquid droplets, which are more easily separated into two liquid phases.

The order of addition of the water and the low solubility extraction solvent to the non-aqueous hydroformylation product composition is not critical. The extraction liquids can be added separately and/or simultaneously, or premixed and then added simultaneously, if desired. As noted hereinbefore, the low solubility extraction solvent can be synthesized in-situ during the hydroformylation step. It is to be understood that the term "added," as it pertains herein to water and any nonpolar hydrocarbon compounds that may have been added as a component of the extraction solvent refers to water and nonpolar hydrocarbon(s) that have been deliberately added to the non-aqueous hydroformylation product composition feed for the purpose of the phase separation process of this invention; in contrast, for example, to nonpolar hydrocarbons that might already be present in said product composition as an ancillary result of the hydroformylation reaction process itself, namely, unreacted olefin (conjugated or unconjugated), in situ produced hydrocarbons, hydrocarbons present as the result of employing impure olefin starting materials, and the like. Such amounts of ancillary nonpolar hydrocarbons, if and when present, may lessen the amount of optionally added nonpolar hydrocarbon compound(s) necessary to achieve a particular desired result.

The mixing and phase separating methods are conducted under extraction conditions that allow for efficient phase separation of the components of the hydroformylation product composition into organic and aqueous phases. Such conditions can be maintained by discharging the syngas saturated hydroformylation reactor effluent into a mixer with or without maintaining pressure, as desired. If it is desired to maintain pressure, a back-pressure regulator can be installed at the outlet of the mixer to maintain the dissolved syngas; or a carbon monoxide-containing gas, a hydrogen-containing gas, or a mixture thereof can be pressurized into the mixer. Suitable carbon monoxide-containing gases include, without limitation, essentially pure gaseous carbon monoxide and mixtures of carbon monoxide with nitrogen, air, inert gases (Ne, Ar, and K), carbon dioxide, or hydrogen (e.g., synthesis gas) Likewise, suitable hydrogen-containing gases include, without limitation, essentially pure hydrogen and mixtures of hydrogen with nitrogen, air, inert gases (Ne, Ar, K), carbon monoxide (e.g., synthesis gas), and carbon dioxide. Advantageously, total pressure in the mixer ranges from greater than about 1 psia (7 kPa or atmospheric pressure) to less than about 800 psia (5,516 kPa). Preferably, the total pressure in the mixer ranges between about 5 psia (34 kPa) and about 600 psia (4,136 kPa). Advantageously, the mixing is conducted at a liquid phase temperature equal to or greater than about 50° C., preferably, greater than about 50° C. and less than about 130° C. A more preferred temperature is about 75° C.+/−15° C. Residence time in the mixer ranges from about 1 minute to about 60 minutes, preferably, from about 1 minute to about 30 minutes. Feed rates of the hydroformylation product and the extraction solvents depend upon the scale of the process and can be determined by a person skilled in the art. Optionally, the liquid medium obtained from the mixer may be forwarded to a coalescer if it is needed to convert emulsion, if any, into a larger droplet liquid medium; and from the coalescer forwarded to a decanter. In the decanter, the phases separate rapidly into an organic phase containing the mixture of formyl-substituted fatty acid triglycerides, optionally one or more aldehydes derived from hydroformylating a $C_{3-6}$ olefin, the extraction solvent having low water solubility and an aqueous phase containing the rhodium-organophosphine ligand complex wherein the ligand is ionically-charged, the free ionically-charged organophosphine ligand, the organic solubilizing agent, and water. The decanter is advantageously operated at a temperature greater than 35° C., and preferably, greater than about 40° C. The decanter is advantageously operated at a temperature less than about 95° C.

More preferably, the decanter is operated at a temperature of about 75° C.+/−15° C. Pressure in the decanter advantageously ranges from about 15 psia (103 kPa) to about 50 psia (345 kPa), but other pressures may be employed, if desired.

The aldehyde containing organic phase can be further extracted with water in a counter-current liquid-liquid extractor. The extractor advantageously operated at a temperature greater than 35° C., and preferably, greater than about 40° C. The extractor advantageously is operated at a temperature less than about 95° C. More preferably, the extractor is operated at a temperature of about 75° C.+/−15° C. Pressure in the extractor advantageously ranges from about 15 psia (103 kPa) to about 60 psia (345 kPa), but other pressures may be employed. If desired, additional ligand may be fed to the liquid-liquid extractor to scavenge residual transition metal.

The low solubility extraction solvent is selected to be compatible with the desired down stream chemistry, so that the aldehyde-containing liquid organic phase ("crude organic phase") from the top of the extractor can be directly subject to the desired down stream reaction conditions to produce a desired application product. When $C_{4-7}$ aldehydes are produced in situ as a co-product of hydroformylation and as the extraction solvent, the organic phase from the extractor is typically subjected to a separation treatment, such as vaporization, to separate and recover the mixture of triglyceride aldehyde products and to recover the $C_{4-7}$ aldehydes as a second product. Any unconverted $C_{3-6}$ olefins may be recycled back to the reactor.

The liquid aqueous phase obtained from the mixer/decanter (crude aqueous phase) containing the rhodium-organophosphine ligand complex wherein the ligand is ionically-charged, optional free ionically-charged organophosphine ligand, the organic solubilizing agent, and water can be treated to remove the water by any conventional method, such as by feeding the crude aqueous phase to any conventional vaporizer-separator. A resulting non-aqueous polar phase containing the rhodium-organophosphine ligand complex, the optional free organophosphine ligand, and the solubilizing agent is preferably recycled back to the hydroformylation reactor of the non-aqueous hydroformylation reaction process in order to achieve a continuous, liquid catalyst recycle. If desired, two or more vaporizer-separators may be employed. For example, a non-aqueous polar phase obtained from the bottoms of the first vaporizer can be employed as the feed to the second vaporizer-separator; and bottoms from the second vaporizer can be recycled to the hydroformylation reactor. Aqueous overhead accumulated from the first and/or second vaporizers consisting essentially of water can be recycled back to the mixer or the extractor.

Additionally, all or a portion of the aqueous polar solution obtained from the liquid-liquid extractor discussed above can have its water removed by the aqueous polar solution to a distillation column, and the resulting non-aqueous polar solution can also be returned to the hydroformylation reactor. A purified water obtained from the distillation can be returned to said liquid-liquid extractor. For efficiency purposes and in order to avoid undue aqueous wetting of the rhodium-organophosphorus ligand complex in the liquid aqueous phase obtained from the mixer-decanter, it may be preferred to employ a different vaporizer-separator, if water is to be removed from any additional liquid polar solution obtained from the liquid-liquid extractor.

With reference to the preceding description, a continuous embodiment of the subject invention is further depicted by referring to the attached Drawing (FIG. 1) wherein syngas (CO and $H_2$) and a mixture of a seed oil mixture of olefinically-mono-unsaturated and olefinically-poly-unsaturated fatty acid esters and optionally a $C_{3-6}$ olefin are fed through lines 1 and 2, respectively, into a hydroformylation zone 101 (alternatively, referred to as an OXO reactor), which contains the transition metal-organophosphine ligand complex catalyst wherein the ligand is ionically-charged, optional free ionically-charged organophosphine ligand, and the polar organic solubilizing agent for said complex and said free ligand, and wherein the non-aqueous hydroformylation of the olefinic compounds takes place, preferably, to a conversion of greater than about 60 up to 100 percent of all unsaturated bonds of said seed oil and greater than about 80 up to 100 percent of unsaturated bonds of said optional $C_{3-6}$ olefin. The resulting non-aqueous hydroformylation product composition comprises a mixture of aldehyde products (mixture of mono-, di-, and tri-formyl-substituted fatty acid triglyceride esters and optionally a $C_{4-7}$ aldehyde), optionally one or more unconverted olefins (conjugated or non-conjugated), the metal-organophosphine ligand complex, optionally, free organophosphine ligand, and the organic solubilizing agent. All or a portion of the non-aqueous hydroformylation product is then continuously withdrawn from the hydroformylation zone 101 and fed via line 4 into the extraction stage comprising a mixer (102), decanter (103), liquid-liquid extractor (104), and various distillation columns (105, 106). Water via line 12 is added to the withdrawn product composition, and thoroughly mixed therewith, in mixer 102, preferably, a static mixer. If the hydroformylation process does not include the $C_{3-6}$ olefin, then an extraction solvent having low water solubility is added to the mixer via line 3. If the hydroformylation process includes a $C_{3-6}$ olefin, then a $C_{4-6}$ aldehyde is obtained, which satisfies the condition in whole or in part for the low solubility extraction solvent. Gas composition and pressure in the mixer can be regulated via gas line 16. The resultant aqueous composition is conveyed via line 4a to a liquid decanter vessel 103, wherein said treated composition settles into two distinct liquid phases, that is, an organic phase comprising the desired aldehyde product(s), unconverted olefin(s) if any, the low solubility extraction solvent, and a liquid aqueous phase comprising the transition metal-organophosphine ligand complex, free organophosphine ligand, the polar organic solubilizing agent for said complex and said free ligand, and water. The crude liquid aldehyde-containing organic phase is removed from the decanter vessel 103 via line 5 and conveyed to a liquid-liquid extractor 104. Polar compounds that might also be present in the liquid aldehyde-containing organic phase can be removed therefrom with the aid of water (and a transition metal scavenger if desired, such as, a corresponding monosulfonated tertiary phosphine metal salt ligand added via line 15 into line 13, in an amount preferably not to exceed what is lost through ligand degradation in the hydroformylation process) added to said liquid-liquid extractor 104 via line 13; and the desired purified organic phase containing aldehyde product is obtained and recovered from said extractor via line 9. Said aldehyde product-containing organic phase so obtained may contain additional non-polar hydrocarbon compounds, such as, unconverted olefins, as well as the polar and nonpolar components of the low solubility extraction solvent; and may be further purified, if desired, in any conventional manner not shown, e.g., by distillation or additional extraction to recover a purified aldehyde product for downstream use. The crude aqueous liquid phase in said decanter 103, containing the transition metal-organophosphine ligand complex and free ligand, can be removed therefrom via line 6 and conveyed to a vaporizer/separator 105 for removal of the water; and the non-aqueous composition obtained therefrom, containing transition metal-organophosphine ligand complex and free organophosphine ligand, can be recycled to the hydroformylation reactor via line 8. The water recovered from said vaporizer/separator 105 can be recycled to the mixer 102 via line 7. Moreover, all or a portion of the aqueous composition obtained from said liquid-liquid extractor 104 via line 10 can be conveyed via line 12 into line 4 containing the non-aqueous hydroformylation product composition for input to the mixer; or alternatively, all or a portion of said aqueous composition from line 10 can be conveyed via line 11 to a distillation column 106, wherein the water can be separated from any of the other polar compounds that may be present, such as, the polar organic solubilizing agent. In general, it is preferred to divide the aqueous composition of said line 10 into two streams, one stream serving as the source of said line 12 and the other as the source of said line 11. The purified water from said distillation column 106 can be reused and returned to said liquid-liquid extractor 104 via line 13, while the polar compounds such as the polar organic solubilizing agent obtained from said distillation column 106 can be recycled to the hydroformylation reactor 101 via line 14.

Figure 1:
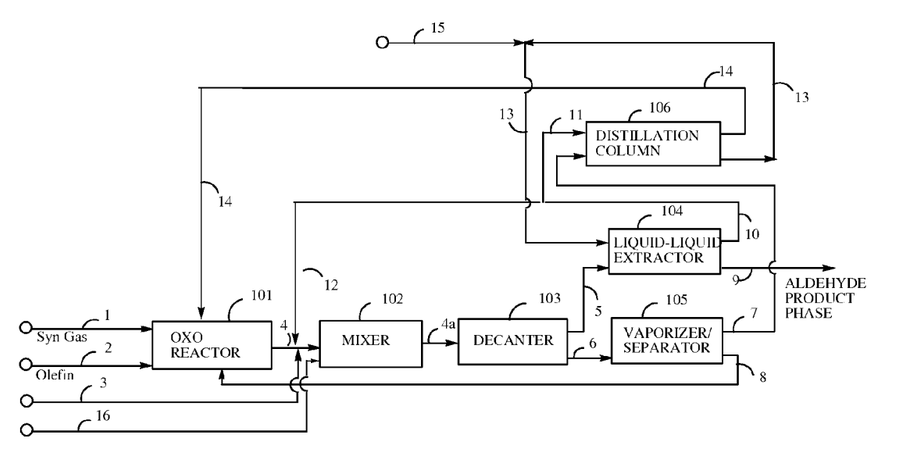
FIG. 1 represents a schematic block flow diagram of an embodiment of the invention as it pertains to separating an aldehyde product comprising a mixture of formyl-substituted fatty acid triglyceride esters from a continuous non-aqueous hydroformylation product composition and to recovering a liquid catalyst-containing stream for recycle to the hydroformylation reactor.

Other embodiments of the FIGURE may be found disclosed herein and/or will be obvious to one skilled in the art. For instance, the source of water added to the non-aqueous hydroformylation product composition via line 12 need not be derived from the aqueous composition of line 10, but can be obtained from a different supply of water from line 13 or some other source not shown. The same is also true of water added to extractor 104 via line 13; it also can be obtained from a supply of water not shown. For example, an initial supply of water is needed at the start up of the process and such may be accomplished by adding said water to line 12 or line 13, or in any other appropriate manner not shown. Moreover, if desired all or part of the aqueous composition of line 10 can first go to vaporizer/separator not shown; the water and vaporized materials collected therefrom going to distillation column 106 and tails from the vaporizer going to vaporizer/separator 105 or some other vaporizer/separator, not shown.

The following examples are set forth to illustrate the invention described herein; but the examples are not to be regarded as limiting thereof. It is to be understood that all parts, percentages and proportions referred to in the examples are by weight unless otherwise indicated.

Preparation of Stock Catalyst Solution

A stock catalyst solution is prepared in a dry box by mixing a solution of dicyclohexylphenylphosphine monosulfonate sodium salt ligand (DCHPPMS-Na) (117.2 g of 20 percent in N-methylpyrrolidone (NMP), 62.269 mmol DCHPPMS-Na) with a solution of $Rh(acac)(CO)_2$ (1.614 g, 6.255 mmol) in NMP (389.69 g). The resulting solution contains 0.127 percent Rh, 4.610 percent DCHPPMS-Na and 95.07 percent NMP. The solution is sealed under nitrogen and constantly stirred. The ligand is prepared in accordance with the procedure described in WO 2004-A1-096744.

EXAMPLE 1

A hydroformylation reactor (Parr pressure reactor, 300 cc) is configured with a dip tube to feed syngas ($CO+H_2$) to the bottom of the reactor, and further equipped with internal coils for controlled water cooling, and with addition cylinders for addition of substrate or water into the reactor under pressure. The reactor is also equipped with a high pressure cylinder (600 cm³, 6000 psia/41.4 MPa) for pressurization with syngas or any other gas to be fed into the reactor. Pressure drop data from this cylinder are used to calculate olefin conversion and reaction rates of the hydroformylation process.

The reactor is cleaned and dried by purging nitrogen. The stock catalyst solution (60.0 ml), prepared as described hereinabove, is transferred into the reactor under nitrogen, followed by addition of degassed high oleic canola oil (130.0 g; >70 percent oleic content). The reactor is purged three times with syngas ($H_2$:CO=1/1) and then pressurized to 390 psia (2689 kPa) (target pressure 400 psia/2758 kPa). The reaction solution is stirred at 1000 rpm and heated to 80° C. The pressure in the reactor is maintained at 400 psia (2758 kPa) by feeding syngas from the high pressure cylinder when the pressure in the reactor drops below the target pressure. Initial pressures in the high pressure cylinder and the reactor are recorded when the temperature is stabilized at 80° C. Pressure drop data are taken through the course of the reaction to determine conversion and rate of reaction.

When the desired conversion, preferably, 92% of the C=C bonds, is reached based on the pressure drop in the high pressure cylinder, the following extraction procedure is carried out. One-half volume (50%) of the reaction solution (~110 ml) is drained into a bottle containing water (25 ml), methyl propyl ketone (50 ml), and 1-octene (40 ml) preheated to 65° C. The bottle is placed in a 65° C. bath and stirred for 5 to 15 minutes to settle out two phases. The crude aqueous phase (bottom phase) is decanted off, and crude organic phase (top phase) is washed with about an equal volume of water 4 times at 65° C. with 5 minutes stirring for each wash. The resulting organic phase is evaporated to obtain a mixture of formyl-substituted fatty acid esters as an aldehyde product. The resulting aldehyde product recovered from the organic phase is analyzed by Neutron Atomic Absorption (NAA) to determine the residual rhodium and by proton ($^1H$) nuclear magnetic spectroscopy ($^1H$ NMR) to determine the conversion of the C=C bonds to formyl groups with the results shown in Table 2.

TABLE 2

Canola Seed Oil Hydroformylation and Aldehyde Product Extraction[a]

| Ex. # | HF[b] T/P (° C./kPa) | Rxn.[b] time (Hr) | Conv[b] % | Extraction Pressure[c] (kPa) | NPH[d] | Clarity of phases and time to achieve thereof Top/Bottom/minutes[e] | Rh in Formyl Product (ppmw) |
|---|---|---|---|---|---|---|---|
| 1 | 80/2758 | 4.6 | 92 | Ambient | 1-Oct | -Clear/Clear/5 | 0.30 ± 0.05 |
| 2 | 80/2758 | 4.6 | 92 | 2758 | 1-Oct | Clear/Clear/5 | 0.24 ± 0.02 |
| 3 | 80/2758 | 4.7 | 92 | Ambient | Hept | -Clear/Clear/30 | 1.05 ± 0.05 |
| 4 | 80/2758 | 4.7 | 92 | 2758 | Hept | -Clear/Clear/30 | 0.42 ± 0.02 |
| 5 | 95/4137 | 1.7 | 93 | 4137 | 1-Oct | Clear/Clear/8 | 0.42 ± 0.03 |
| 6 | 95/4137 | 1.7 | 93 | 4137 | Hept | -Clear/-Clear/10 | 0.48 ± 0.03 |

[a]Extraction employs water ($H_2O$/NMP (vol/vol) = 0.85, NMP = N-methyl pyrrolidone), methyl propyl ketone (MPK, MPK/Oil (vol/vol) = 0.70), and a non-polar hydrocarbon (NPH, NPH/Oil (vol/vol) = 0.57).
[b]HF = hydroformylation; Rxn time = reaction time for hydroformylation; Conversion is given as percentage of C=C double bonds converted.
[c]"Ambient" means the mixing is conducted outside the reactor in a glass bottle.
[d]"1-Oct" = 1-octene; "Hept" = heptane
[e]"Clear" means clear phases are obtained in the initial phase separation and the four water washes. "-Clear" means cloudiness is observed in the phase in one or more stages of phase separations. The time (minutes) is the longest time to achieve clarity in any one stage phase separation, either the initial or one of the water washes. Clarity is measured visually.

EXAMPLE 2

Referring to Example 1 following the hydroformylation step, the 50 volume percent of the hydroformylation product composition remaining in the hydroformylation reactor is treated in the following manner. The stirring rate is reduced to 600 rpm; the temperature is lowered to 75° C.; and 100 psia (689 kPa) syngas pressure in the reactor is slowly vented. Degassed deionized water (25 ml) is transferred into the substrate addition cylinder under nitrogen. The cylinder is purged with syngas three times and then pressurized to the target pressure (400 psia/2758 kPa). Water in the substrate cylinder is pressurized into the reactor; the temperature is lowered to 65° C.; and stirring is continued at 600 rpm for 15 min. The resulting mixture is drained into a bottle containing methyl propyl ketone (50 ml) and 1-octene (40 ml) which is preheated to 65° C. The bottle is placed in a 65° C. bath and stirred for 5 to 15 minutes to settle out two phases. The bottom phase (crude aqueous phase) is decanted off, and the top phase (crude organic phase) is washed with about an equal volume of water 4 times at 65° C. with 5 minutes stirring for each wash. The resulting organic phase is evaporated to obtain a mixture of formyl-substituted fatty acid esters as an aldehyde product. The products are analyzed for rhodium and analyzed by $^1$H NMR with the results shown in Table 2.

EXAMPLE 3

The procedure of Example 1 is repeated, with the exception that heptane replaces 1-octene as the nonpolar hydrocarbon solvent. Results are shown in Table 2.

EXAMPLE 4

The procedure of Example 2 is repeated, with the exception that heptane replaces 1-octene as the nonpolar hydrocarbon solvent. Results are shown in Table 2.

EXAMPLE 5

The general procedure of Example 1 is repeated, with the exception that the hydroformylation process conditions are the following: 100 g high oleic canola oil, 95° C., 600 psia (4137 kPa), and 46 ml stock catalyst solution. In addition, after hydroformylation water (38 ml) is pressurized into the reactor and mixed with the entire reactor contents, not only 50 percent of the reactor contents. The resulting mixture is drained into two bottles and allowed to settle into two phases with the results shown in Table 2.

EXAMPLE 6

The general procedure of Example 2 is repeated, with the exception that the hydroformylation process conditions are the following: 100 g high oleic canola oil, 95° C., 600 psia (4137 kPa), and 46 ml stock catalyst solution. In addition, water (38 ml) is pressurized into the reactor and mixed with the entire reactor contents, not only 50 percent of the reactor contents. The extraction solvent is heptane, rather than 1-octene. The resulting mixture is drained into two bottles and allowed to settle into two phases with the results shown in Table 2.

EXAMPLE 7

The procedure of Example 1 is repeated, with the exception that soybean oil replaces canola oil, and the hydroformylation temperature and pressure are 85° C. and 600 psia (4137 kPa), respectively. Results are set forth in Table 3.

TABLE 3

Soybean Seed Oil Hydroformylation and Aldehyde Product[a]

| Ex. # | HF[b] T/P (° C./kPa) | Rxn.[b] time (Hr) | Conv.[b] % | Extraction Pressure[c] | NPH[d] | Clarity of phases and time to achieve thereof Top/Bottom/minutes[e] | Rh in Formyl Product (ppmw) |
|---|---|---|---|---|---|---|---|
| 7 | 85/4137 | 6.4 | 97.2 | Ambient | 1-Oct | Clear/Clear/20 | 0.74 ± 0.05 |
| 8 | 85/4137 | 6.4 | 97.2 | 4137 | 1-Oct | Clear/Clear/5 | 0.51 ± 0.02 |
| 9 | 80/4137 | 16 | 100.0 | 4137 | 1-Oct | Clear/Clear/3 | 0.84 ± 0.05 |
| 10 | 80/4137 | 16 | 100.0 | 4137 | Hept | Clear/Clear/3 | 0.84 ± 0.05 |
| 11 | 95/4137 | 2.6 | 95.5 | 4137 | 1-Oct | Clear/Clear/2 | 0.54 ± 0.03 |
| 12 | 95/4137 | 2.6 | 95.5 | 4137 | Hept | Clear/Clear/2 | 0.59 ± 0.03 |

[a]Extraction employs water (H$_2$O/NMP (vol/vol) = 0.85, NMP = N-methyl pyrrolidone), methyl propyl ketone (MPK, MPK/Oil (vol/vol) = 0.70), and a non-polar hydrocarbon (NPH, NPH/Oil (vol/vol) = 0.57).
[b]HF = hydroformylation; Rxn time = reaction time for hydroformylation; Conversion is given as percentage of C═C double bonds converted.
[c]"Ambient" means the mixing is conducted outside the reactor in a glass bottle.
[d]"1-Oct" = 1-octene; "Hept" = heptane
[e]"Clear" means clear phases are obtained in the initial phase separation and the four water washes. The time (minutes) is the longest time to achieve the clarity in any one stage phase separation, either the initial or one of the water washes. Clarity is determined visually.

EXAMPLE 8

The procedure of Example 2 is repeated, with the exception that soybean oil replaces canola oil, and the hydroformylation temperature and pressure are 85° C. and 600 psia (4137 kPa), respectively. Results are set forth in Table 3.

EXAMPLES 9-12

The general procedure of Example 1 is repeated in four more examples of hydroformylation using soybean oil and subsequent extraction, under the process conditions and with the results shown in Table 3.

EXAMPLE 13

The general procedure of Example 2 is repeated, with the exception that the hydroformylation process conditions are the following: 80 g high oleic canola oil, 37 ml stock catalyst solution, at 80° C. under 400 psia (2756 kPa) syngas pressure. The reaction is run for 4.3 hours. Following the hydroformylation, water (31 ml=0.85 vol per vol NMP) is pressurized into the reactor and mixed with the entire reactor contents at 65° C. under 400 psia (2756 kPa) syngas pressure, and the entire resulting mixture is drained into one bottle containing 120 ml diisopropyl ether (DIPE, DIPE/oil (vol/vol)=1.38) preheated to 65° C. and functioning as a single component low solubility extraction solvent. Four water washes are carried out as described in Experiment 2, except that 100 ml of 65° C. water are used for each wash. The aldehyde product is isolated from the organic phase and analyzed by NAA and proton NMR with the results shown in Table 4. The product is also analyzed by X-ray fluorescence to determine the residual phosphorus in the product.

TABLE 4

High Oleic and Soybean Oil Hydroformylation and Aldehyde Product Extraction[a]

| Exp. # | Oil | HF Rxn Time[b] (Hr) | Conversion Mol %[b] | Clarity of phases and time to achieve thereof Top/Bottom/minutes[c] | Rh in formyl product (ppmw) | Phosphorus in product (ppmw) |
|---|---|---|---|---|---|---|
| 13 | High Oleic | 4.3 | 90.4 | Clear/Clear/7 | 0.29 ± 0.01 | 4 ± 2 |
| 14 | High Oleic | 4.7 | 91.5 | Clear/Clear/5 | 0.32 ± 0.01 | 4 ± 2 |
| 15 | Soy | 6.7 | 86.7 | Cloudy/Clear/20 | 0.56 ± 0.01 | N/A |

[a]Extraction employs water and diisopropyl ether as the extraction solvent.
[b]"HF Rxn Time" is the hydroformylation reaction time. Conversion is given as percentage of C═C double bonds converted.
[c]The time (minutes) is the longest time to achieve the clarity in one phase separation, either the initial or one of the water washes. Clarity is determined visually.

EXAMPLE 14

Example 13 is repeated, except that the reaction time is 4.7 hours. Results are shown in Table 4.

EXAMPLE 15

Example 13 is repeated, with the exception that Crisco™ soybean oil (100 g) replaces the high oleic canola oil and the following quantities are used: 46 ml stock catalyst solution, 38 ml water for post reaction mixing, and 152 ml diisopropyl ether for extraction. The results are shown in Table 4.

EXAMPLES 16-22

Example 15 is repeated for each of additional Examples 16 through 22, with the exception that the reaction is carried out to lower conversion, and a different extraction solvent or solvent mixture is used in each example. The solvents, process conditions, and results are shown in Table 5.

TABLE 5

Soybean Oil Hydroformylation and Aldehyde Product Extraction[a]

| Ex # | Extraction Solvent (ES) | ES/Oil (v/v)[b] | HF Rxn time (hr)[c] | Conv[c] C═C % | Clarity of phases and time to achieve thereof Top/Bottom/minutes[d] | Rh in formyl product ppmw |
|---|---|---|---|---|---|---|
| 16 | Diisopropyl ether (DIPE) | 1.4 | 2.6 | 71 | -Clear/Clear/14 | 0.51 ± 0.01 |
| 17 | Ethyl butyrate | 1.4 | 2.3 | 69 | -Clear/Clear/3 | 0.36 ± 0.01 |
| 18 | Methyl butyrate | 1.2 | 2.4 | 71 | -Clear/Clear/13 | 0.50 ± 0.01 |
| 19 | Ethyl propionate | 1.0 | 2.4 | 70 | -Clear/Clear/15 | 1.13 ± 0.01 |
| 20 | Diethyl carbonate (DEC) | 1.0 | 2.4 | 71 | -Clear/Clear/25 | 1.19 ± 0.01 |
| 21 | DEC Heptane | 1.0 0.46 | 2.4 | 71 | -Clear/Clear/21 | 0.41 ± 0.01 |
| 22 | DEC DIPE | 0.73 0.73 | 2.4 | 71 | -Clear/Clear/30 | 0.43 ± 0.01 |

[a]Extraction employs water and extraction solvent (ES) shown.
[b]"EX/Oil" = volume ratio of the extraction solvent to oil.
[c]"HF Rxn Time" = hydroformylation reaction time; 80° C.; 400 psia (2756 kPa); "Conv C═C %" = Mol % of C═C converted to Formyl
[d]"Clear" means clear phases are obtained in the initial phase separation and the four water washes. "-Clear" means cloudiness is observed in the phase in one or more stages of phase separations. The time (minutes) is the longest time to achieve the clarity in any one stage phase separation, either the initial or one of the water washes. Clarity is determined visually.

EXAMPLE 23

A hydroformylation process is conducted according to the procedure of Example 1 using the stock Rh-catalyst solution (55.2 ml) and a degassed feed mixture comprising high oleic canola oil (30.0 g) and 1-hexene (30 g). The reactor is purged three times with syngas and then pressurized to 390 psia (2068 kPa) (target pressure 400 psia/2758 kPa). The reaction solution is stirred at 1000 rpm and heated to 85° C. Pressure in the reactor is maintained at the 400 psia (2068 kPa) by feeding syngas from the high pressure cylinder when pressure in the reactor drops below the target pressure. Initial pressure in the high pressure cylinder and the reactor are recorded when the temperature is stabilized at 80° C. Pressure drop data are taken through the course of the reaction to determine conversion and reaction rate. Degassed deionized water (23 ml) is transferred into a substrate addition cylinder under nitrogen. The cylinder is purged with syngas three times and then pressurized to the target pressure. The reaction is run for 393 minutes and then the following extraction procedure is conducted.

The stir rate is reduced to 600 rpm; the temperature is lowered to 75° C.; and 689 psia (4750 kPa) syngas pressure in the reactor is slowly vented. The water in the substrate cylinder is pressurized into the reactor; the temperature is lowered to 65° C. and continued to stir at 600 rpm for 15 minutes. The mixture is drained into a 200 ml bottle under nitrogen. The bottle is then placed in a 65° C. bath to settle into two phases. The aqueous bottom phase is decanted after settling and the crude organic top phase is washed with water (4×50 ml) at 65° C. with 5 minutes stirring for each wash. The resulting aldehyde product recovered from the organic phase is determined by Neutron Atomic Absorption (NAA) to contain 0.52±0.02 ppmw rhodium. X-ray fluorescence analysis shows that the formyl product contains 5±2 ppmw phosphorus. $^1$H NMR analysis shows that 1-hexene is completely converted to aldehydes (heptanals) and the C=C double bonds of the soy oil are 95 percent converted to aldehydes. The heptanals prepared in situ during hydroformylation serve as the extraction solvent having low water solubility.

What is claimed is:

1. An extraction process of a hydroformylation product composition to separate therefrom an aldehyde product and to recover a hydroformylation catalyst, the process comprising mixing a non-aqueous hydroformylation product composition comprising a mixture of formyl-substituted fatty acid triglyceride esters, a transition metal-organophosphine ligand complex wherein the organophosphine ligand is ionically charged, optionally free ionically-charged organophosphine ligand, and a polar organic solubilizing agent for said complex and said free ligand with water and an extraction solvent having low water solubility, under conditions sufficient to obtain by one or more stages of phase separation an organic phase comprising the mixture of formyl-substituted fatty acid triglyceride esters and the extraction solvent having low water solubility and an aqueous phase comprising the transition metal-organophosphine ligand complex wherein the ligand is ionically-charged, optionally free ionically-charged organophosphine ligand, the polar organic solubilizing agent, and water.

2. The process of claim 1 wherein the low solubility extraction solvent comprises a single polar compound or a mixture of polar compounds each having a solubility in water ranging from 0.10 gram to 1.8 grams per 100 grams water; or the extraction solvent comprises a mixture of one or more polar compounds and one or more nonpolar compounds wherein the mixture has a solubility in water ranging from greater than 1.8 to 7 grams per 100 grams water.

3. The process of claim 1 wherein the mixture of formyl-substituted fatty acid triglyceride esters is derived from hydroformylation of a mixture of triglyceride esters of fatty acids, each fatty acid having from 12 to 24 carbon atoms.

4. The process of any one of claim 1 wherein the hydroformylation product composition is derived from the hydroformylation of a seed oil selected from castor, soybean, olive, peanut, rapeseed, corn, sesame, cottonseed, canola, safflower, sunflower, and high oleic oils, as well as genetically-modified variations of the aforementioned oils, and mixtures thereof.

5. The process of claim 1 wherein each component of the low solubility extraction solvent has a normal boiling point greater than 60° C. and less than 175° C.

6. The process of claim 1 wherein the low solubility extraction solvent is selected from $C_{4-7}$ aldehydes, $C_{4-8}$ esters, $C_{4-8}$ ketones, $C_{4-8}$ ethers, $C_{7-12}$ polar aromatic solvents, and mixtures thereof.

7. The process of claim 6 wherein the low solubility extraction solvent is a $C_{4-7}$ aldehyde that is synthesized in situ in a hydroformylation process from which the hydroformylation product composition is derived.

8. The process of claim 1 wherein from 2 to 60 percent by weight of water is mixed in the extraction, based on the total weight of the non-aqueous hydroformylation product composition.

9. The process of claim 1 wherein from 20 to 150 percent by weight low solubility extraction solvent is mixed in the extraction, based on the total weight of the non-aqueous hydroformylation product composition.

10. The process of claim 1 wherein the extraction and/or mixing is conducted at a temperature equal to or greater than 50° C. and less than 130° C. and a pressure ranging from greater than 1 psia (7 kPa) to less than 800 psia (5516 kPa).

11. The process of claim 1 wherein the organic solubilizing agent is N-methyl pyrrolidone.

12. The process of claim 1 wherein the organophosphorus ligand is represented by the following formula:

wherein $R^1$ and $R^2$ each individually represent a radical containing from 1 to 30 carbon atoms selected from the group consisting of alkyl, aryl, alkaryl, aralkyl and alicyclic radicals; wherein $R^3$ represents a divalent alkylene radical having from 2 to 12 carbon atoms, or a divalent 1,3-phenylene radical; wherein M represents a metal cation selected from the group consisting of alkali and alkaline earth metals; and wherein n has a value of 1 or 2 corresponding to the valence of the particular metal cation represented by M.

13. The process of claim 1 wherein the organophosphorus ligand is represented by the following formula:

wherein $R^1$ and $R^2$ each individually represent a radical containing from 1 to 30 carbon atoms selected from the group consisting of alkyl, aryl, alkaryl, aralkyl and alicyclic radicals; wherein M represents a metal cation selected from the group consisting of alkali and alkaline earth metals; and wherein n has a value of 1 or 2 corresponding to the valance of the particular metal cation represented by M.

14. The process of claim 1 wherein the phase separation provides for separation of greater than 95 weight percent of the aldehyde product(s) based on the weight of the total aldehyde product(s) in the hydroformylation product composition, and a separation of greater than 98 weight percent of the free organophosphine ligand, based on total weight of the organophosphine ligand in the hydroformylation product composition.

15. An integrated process of hydroformylating a seed oil in its triglyceride form and extracting a hydroformylation product composition derived therefrom to separate an aldehyde product and to recover a hydroformylation catalyst, the process comprising:
(a) hydroformylating a seed oil comprising a mixture of olefinically-unsaturated fatty acid triglyceride esters with carbon monoxide and hydrogen in the presence of a transition metal-organophosphine ligand complex catalyst wherein the organophosphine ligand is ionically-charged, optionally free ionically-charged organophosphine ligand, and a polar organic solubilizing agent for said complex and said optional free ligand, in a hydroformylation reactor under reaction conditions sufficient to obtain a non-aqueous hydroformylation product composition comprising a mixture of formyl-substituted fatty acid triglyceride esters, the transition metal-organophosphine ligand complex wherein the ligand is ionically-charged, optionally free ionically-charged organophosphine ligand, and the polar organic solubilizing agent for said complex and said optional free ligand; and thereafter
(b) mixing the non-aqueous hydroformylation product composition with water and an extraction solvent having low water solubility under conditions sufficient to obtain by one or more stages of phase separation an organic phase comprising the mixture of formyl-substituted fatty acid triglyceride esters and the extraction solvent having low water solubility and an aqueous phase comprising the transition metal-organophosphine ligand complex wherein the ligand is ionically-charged, optionally the free ionically-charged organophosphine ligand, the polar organic solubilizing agent, and water.

16. An integrated process of hydroformylating a seed oil in its triglyceride form and extracting a hydroformylation product composition derived therefrom to separate an aldehyde product and to recover a hydroformylation catalyst, the process comprising:
(a) hydroformylating a seed oil comprising a mixture of olefinically unsaturated fatty acid triglyceride esters and simultaneously hydroformylating a $C_{3-6}$ olefin with carbon monoxide and hydrogen in the presence of a transition metal-organophosphine ligand complex catalyst wherein the organophosphine ligand is ionically-charged, optionally free ionically-charged organophosphine ligand, and a polar organic solubilizing agent for said complex and said optional free ligand, in a hydroformylation reactor under reaction conditions sufficient to obtain a non-aqueous hydroformylation product composition comprising a mixture of formyl-substituted fatty acid triglyceride esters, a $C_{4-7}$ aldehyde capable of serving as an extraction solvent having low water solubility, the transition metal-organophosphine ligand complex wherein the ligand is ionically-charged, optionally free ionically-charged organophosphine ligand, and the polar organic solubilizing agent for said complex and said optional free ligand; and thereafter
(b) mixing the non-aqueous hydroformylation product composition with water under conditions sufficient to obtain by one or more stages of phase separation an organic phase comprising the mixture of formyl-substituted fatty acid triglyceride esters and the $C_{4-7}$ aldehyde serving as the extraction solvent having low water solubility and an aqueous phase comprising the transition metal-organophosphine ligand complex wherein the ligand is ionically-charged, optionally the free ionically-charged organophosphine ligand, the polar organic solubilizing agent, and water.

17. The process of claim 15 wherein the extraction solvent comprises a single polar compound or a mixture of polar compounds each having a solubility in water ranging from 0.10 gram to 1.8 grams per 100 grams water; or wherein the extraction solvent comprises a mixture of one or more polar compounds and one or more nonpolar compounds wherein the mixture has a solubility in water ranging from greater than 1.8 grams to 7 grams per 100 grams water.

18. The process of claim 15 further comprising (c) removing water from the aqueous phase and recycling a resulting non-aqueous polar phase comprising the transition metal-organophosphine ligand complex wherein the ligand is ionically-charged, optionally free ionically-charged organophosphine ligand, and the polar organic solubilizing agent back to the hydroformylation step (a).

19. The process of any one of claim 15 wherein the hydroformylation step (a) is conducted at a transition metal concentration ranging from 10 ppm to 800 ppm, calculated as transition metal and based on the weight of the non-aqueous hydroformylation reaction medium.

20. The process of claim 1 wherein the low solubility extraction solvent is selected from the group consisting of diisopropyl ether, ethyl butyrate, methyl butyrate, mixtures of methyl propyl ketone with octenes and/or heptanes, and mixtures of ethyl acetate with octenes and/or heptanes.

* * * * *